(12) United States Patent
Kumano

(10) Patent No.: US 10,852,312 B2
(45) Date of Patent: Dec. 1, 2020

(54) DETERMINATION METHOD OF BLOOD SAMPLE, BLOOD SAMPLE ANALYZER, AND COMPUTER PROGRAM

(71) Applicant: SYSMEX CORPORATION, Kobe (JP)

(72) Inventor: Osamu Kumano, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 228 days.

(21) Appl. No.: 16/003,560

(22) Filed: Jun. 8, 2018

(65) Prior Publication Data

US 2018/0356433 A1 Dec. 13, 2018

(30) Foreign Application Priority Data

Jun. 9, 2017 (JP) ................................. 2017-114568

(51) Int. Cl.
*G01N 33/86* (2006.01)
*G01N 33/96* (2006.01)
*G01N 33/49* (2006.01)

(52) U.S. Cl.
CPC ............. *G01N 33/86* (2013.01); *G01N 33/96* (2013.01); *G01N 33/4905* (2013.01); *G01N 2496/05* (2013.01)

(58) Field of Classification Search
CPC .... G01N 2496/05; G01N 33/86; G01N 33/96; G01N 33/49; G01N 33/4905
USPC ................. 436/63, 69, 164; 435/13; 422/73; 600/369
See application file for complete search history.

(56) References Cited

U.S. PATENT DOCUMENTS

| | | | | |
|---|---|---|---|---|
| 10,132,819 B2* | 11/2018 | Kumano | ............ | G01N 33/4905 |
| 10,215,766 B2* | 2/2019 | Shima | ..................... | G01N 33/86 |
| 10,578,628 B2* | 3/2020 | Ieko | ........................ | G01N 21/82 |
| 2004/0091952 A1 | 5/2004 | Okuda | | |
| 2011/0129862 A1* | 6/2011 | Nakamura | ............. | G01N 33/86 |
| | | | | 435/13 |
| 2011/0159597 A1* | 6/2011 | Yoshida | ................... | C12Q 1/56 |
| | | | | 436/69 |

(Continued)

FOREIGN PATENT DOCUMENTS

WO     2016/136558     * 9/2016

OTHER PUBLICATIONS

Lindhoff-Last et al. Clinical Appl. Thrombosis/Hemostasis, vol. 8(2), 2002, pp. 163-167.*

(Continued)

*Primary Examiner* — Maureen Wallenhorst
(74) *Attorney, Agent, or Firm* — Metrolex IP Law Group, PLLC

(57) ABSTRACT

A determination method of a blood sample may include: measuring, with a first coagulation time measurement reagent and a second coagulation time measurement reagent which contain phospholipids at different concentrations, coagulation times of a blood sample of a subject, coagulation times of a normal blood sample, and coagulation times of a mixed sample including the blood sample of the subject and the normal blood sample; acquiring a first index value and a second index value based on the coagulation times; and determining whether the blood sample of the subject is a blood sample containing a direct anticoagulant based on the first index value and the second index value.

18 Claims, 14 Drawing Sheets

(56) References Cited

U.S. PATENT DOCUMENTS

2014/0127725 A1* 5/2014 Ieko .................. G01N 33/86
  435/13
2014/0295470 A1* 10/2014 Okuda ................ G01N 33/86
  435/13

OTHER PUBLICATIONS

Kumano et al. Thrombosis Research, vol. 143, May 10, 2016, pp. 53-57.*

* cited by examiner

FIG. 8

| ▽ | D | STATUS | RACK No.-POSITION | SAMPLE No. | START TIME | END TIME | FSL C sec | FSL C sec | SP C sec | LA1 1-1 sec | LA2 1-1 sec |
|---|---|---|---|---|---|---|---|---|---|---|---|
| | | | 000012-01 | FII 20 | 14:29 | 14:38 | | | | 54.2 | 48.9 |
| | | | 000012-02 | FII 20 1-1 | 14:30 | 14:39 | | | | 41.5 | 39.1 |
| | | | 000012-03 | FII 10 | 14:30 | 14:39 | | | | 66.3 | 58.3 |
| | | | 000012-04 | FII 10 1-1 | 14:31 | 14:40 | | | | 42.3 | 39.8 |
| | | | 000012-05 | FII 5 | 14:32 | 14:40 | | | | 82.3 | 70.3 |
| | | | 000012-06 | FII 5 1-1 | 14:32 | 14:41 | | | | 42.6 | 40.1 |
| | | | 000012-07 | FII 2.5 | 14:33 | 14:42 | | | | 103.6 | 86.7 |
| | | | 000012-08 | FII 2.5 1-1 | 14:33 | 14:42 | | | | 42.8 | 40.0 |
| | | | 000012-09 | FII 1 | 14:34 | 14:43 | | | | *138.2 | 115.3 |
| | | Review | 000012-10 | FII 1 1-1 | 14:35 | 14:43 | | | | 42.9 | 40.2 |
| | | | 000013-01 | FV 20 | 14:39 | 14:48 | | | | 57.0 | 53.7 |
| | | | 000013-02 | FV 20 1-1 | 14:40 | 14:48 | | | | 42.7 | 40.1 |
| | | | 000013-03 | FV 10 | 14:40 | 14:49 | | | | 68.4 | 64.4 |
| | | | 000013-04 | FV 10 1-1 | 14:41 | 14:50 | | | | 43.5 | 41.2 |
| | | | 000013-05 | FV 5 | 14:42 | 14:50 | | | | 83.6 | 78.6 |
| | | | 000013-06 | FV 5 1-1 | 14:42 | 14:51 | | | | 43.9 | 41.4 |
| | | | 000013-07 | FV 2.5 | 14:43 | 14:51 | | | | 101.6 | 95.0 |
| | | | 000013-08 | FV 2.5 1-1 | 14:43 | 14:52 | | | | 44.4 | 42.1 |
| | | | 000013-09 | FV 1 | 14:44 | 14:53 | | | | 126.4 | 117.7 |
| | | | 000013-10 | FV 1 1-1 | 14:45 | 14:53 | | | | 44.4 | 42.0 |

DETERMINATION METHOD OF BLOOD SAMPLE, BLOOD SAMPLE ANALYZER, AND COMPUTER PROGRAM

CROSS REFERENCE TO RELATED APPLICATIONS

This application claims priority from prior Japanese Patent Application No. 2017-114568 filed with the Japan Patent Office on Jun. 9, 2017, the entire contents of which are incorporated herein by reference.

BACKGROUND

The disclosure relates to a determination method of a blood sample. The disclosure also relates to a device for an analysis of a blood sample and to a computer program.

Lupus anticoagulant (LA) is an autoantibody that inhibits a phospholipid-dependent coagulation reaction, which is detected from a patient with an antiphospholipid antibody syndrome who presents with thrombosis or pregnancy complications. The LA inhibits phospholipids necessary for phospholipid-dependent coagulation reactions, and a coagulation time is prolonged in the case of blood collected from a patient who is LA-positive. In the meantime, a coagulation time is also prolonged in the case of blood collected from a patient dosed with an anticoagulant such as Warfarin. Accordingly, it is necessary to discriminate between a blood sample containing the LA and a blood sample containing an anticoagulant in order to accurately detect a blood sample of an LA-positive patient. However, it is difficult to discriminate between these samples in an ordinary coagulation test.

When a patient is suspected to be LA-positive, a mixing test takes place as a test for the LA. In the mixing test, plasma of a subject is mixed with normal plasma, and a coagulation time of the obtained mixed plasma is measured. When the subject is an LA-positive patient, prolongation of the coagulation time is not improved by conducting the mixing test. Furthermore, there is known a method of detecting the LA in which an index value such as an Index of Circulating Anticoagulant (ICA) and a Lupus Ratio (LR) value for quantitatively evaluating a result of a mixing test is calculated from the coagulation time of each of the plasma of the subject, the normal plasma, and the mixed plasma so as to detect the LA based on the index value. Meanwhile, in a confirmation test for the LA, it is confirmed whether or not the prolongation of the coagulation time depends on the phospholipid. Specifically, the sample containing the LA is detected by measuring the coagulation time while using two types of coagulation time measurement reagents with different phospholipid concentrations, and confirming the prolongation of the coagulation time dependent on the phospholipid concentration based on a ratio of the coagulation time obtained by using the respective reagents.

For example, US Patent Application No. 2004/091952 (Patent Document 1) discloses discriminability between a sample containing the LA and a sample containing Warfarin by a combination of a mixing test and a confirmation test for phospholipid dependency. Specifically, the coagulation time of each of the mixed plasma and the normal plasma is measured by using two types of the coagulation time measurement reagents with different phospholipid concentrations, and the plasma of the LA-positive patient is discriminated from the plasma of the patient dosed with Warfarin based on the LA values calculated from the coagulation time of these plasmas.

While Warfarin has heretofore been used commonly as the anticoagulant, other new anticoagulants with different action mechanisms from that of Warfarin have also been put into use in recent years. Such an anticoagulant binds to a coagulation factor and exhibits an action to directly inhibit a coagulation reaction mediated by the coagulation factor. The anticoagulant that has the action to directly inhibit the coagulation reaction is hereinafter referred to as a "direct anticoagulant" or a "DAC". The coagulation time is also prolonged in the case of a blood sample of a patient dosed with the DAC. However, it has been difficult to discriminate between a sample containing the DAC and a sample containing the LA by using a conventional method. If the blood sample of the subject dosed with the DAC is determined as the sample containing the LA by mistake, the subject is liable to undergo an excessive anticoagulation therapy. Such an excessive anticoagulation therapy increases a hemorrhage risk. For this reason, it is clinically important to discriminate between the blood sample containing the DAC and the blood sample containing the LA.

Meanwhile, in view of testing costs and the like, this discrimination preferably does not require a special reagent or the like for detecting the DAC. Hence, a development of a measure to enable the discrimination between the blood sample containing the DAC and the blood sample containing the LA by use of the conventional coagulation time measurement reagents is expected.

SUMMARY

A determination method of a blood sample according to one or more aspects may include: acquiring: a first coagulation time including a coagulation time of a blood sample of a subject; a second coagulation time including a coagulation time of a normal blood sample; and a third coagulation time including a coagulation time of a mixed sample including the blood sample of the subject and the normal blood sample; acquiring: a fourth coagulation time including a coagulation time of the blood sample of the subject; a fifth coagulation time including a coagulation time of the normal blood sample; and a sixth coagulation time including a coagulation time of the mixed sample; acquiring: a first index value based on the first coagulation time, the second coagulation time, and the third coagulation time; and a second index value based on the fourth coagulation time, the fifth coagulation time, and the sixth coagulation time; and determining whether the blood sample of the subject is a blood sample containing a direct anticoagulant based on the first index value and the second index value. The first coagulation time, the second coagulation time, and the third coagulation time may be coagulation times measured by using a first coagulation time measurement reagent. The fourth coagulation time, the fifth coagulation time, and the sixth coagulation time may be coagulation times measured by using a second coagulation time measurement reagent. The first coagulation time measurement reagent may contain a phospholipid and the second coagulation time measurement reagent contains a phospholipid at a concentration higher than a concentration of the phospholipid in the first coagulation time measurement reagent.

A blood sample analyzer according to one or more aspects may include: a measurement part that prepares a measurement specimen containing a blood sample and a coagulation time measurement reagent, and acquire coagulation time by using the prepared measurement specimen; and an analysis part that analyzes the blood sample based on the coagulation time. The measurement part may measure a first coagulation time with preparing a first measurement specimen from a blood sample of a subject and from a first coagulation time measurement reagent, measure a second coagulation time with preparing a second measurement specimen from a normal blood sample and from the first coagulation time measurement reagent, and measure a third coagulation time with preparing a third measurement specimen from a mixed sample obtained by mixing the blood sample of the subject with the normal blood sample and from the first coagulation time measurement reagent. The measurement part may measure a fourth coagulation time with preparing a fourth measurement specimen from the blood sample of the subject and from a second coagulation time measurement reagent, measure a fifth coagulation time with preparing a fifth measurement specimen from the normal blood sample and from the second coagulation time measurement reagent, and measure a sixth coagulation time with preparing a sixth measurement specimen from the mixed sample and from the second coagulation time measurement reagent. The analysis part may acquire a first index value based on the first coagulation time, the second coagulation time, and the third coagulation time, and acquire a second index value based on the fourth coagulation time, the fifth coagulation time, and the sixth coagulation time. The first coagulation time measurement reagent may contain a phospholipid. The second coagulation time measurement reagent may contain a phospholipid at a concentration higher than a concentration of the phospholipid in the first coagulation time measurement reagent.

A blood sample analyzer according to one or more aspects may include: a measurement part that prepares a measurement specimen containing a blood sample and a coagulation time measurement reagent, and acquire coagulation time by using the prepared measurement specimen; and an analysis part that analyzes the blood sample based on the coagulation time. The measurement part may measure a first coagulation time with preparing a first measurement specimen from a blood sample of a subject and from a first coagulation time measurement reagent, and measure a third coagulation time with preparing a third measurement specimen from a mixed sample obtained by mixing the blood sample of the subject with a normal blood sample and from the first coagulation time measurement reagent. The measurement part may measure a fourth coagulation time with preparing a fourth measurement specimen from the blood sample of the subject and from a second coagulation time measurement reagent, and measure a sixth coagulation time with preparing a sixth measurement specimen from the mixed sample and from the second coagulation time measurement reagent. The analysis part may acquire a first index value based on the first coagulation time, the third coagulation time, and a second coagulation time including a predetermined coagulation time of the normal blood sample with the first coagulation time measurement reagent. The analysis part may acquire a second index value based on the fourth coagulation time, the sixth coagulation time, and a fifth coagulation time including a predetermined coagulation time of the normal blood sample with the second coagulation time measurement reagent. The first coagulation time measurement reagent may contain a phospholipid. The second coagulation time measurement reagent may contain a phospholipid at a concentration higher than a concentration of the phospholipid in the first coagulation time measurement reagent.

A non-transitory computer-readable recording medium, according to one or more aspects, storing a program causing a computer to perform operations may comprise: acquiring: a first coagulation time including a coagulation time of a blood sample of a subject; a second coagulation time including a coagulation time of a normal blood sample; and a third coagulation time including a coagulation time of a mixed sample including the blood sample of the subject and the normal blood sample; acquiring: a fourth coagulation time including a coagulation time of the blood sample of the subject; a fifth coagulation time including a coagulation time of the normal blood sample; and a sixth coagulation time including a coagulation time of the mixed sample; acquiring: a first index value based on the first coagulation time, the second coagulation time, and the third coagulation time; and a second index value based on the fourth coagulation time, the fifth coagulation time, and the sixth coagulation time. The first coagulation time, the second coagulation time, and the third coagulation time may be coagulation times measured by using a first coagulation time measurement reagent. The fourth coagulation time, the fifth coagulation time, and the sixth coagulation time may be coagulation times measured by using a second coagulation time measurement reagent. The first coagulation time measurement reagent may contain a phospholipid. The second coagulation time measurement reagent may contain a phospholipid at a concentration higher than a concentration of the phospholipid in the first coagulation time measurement reagent.

According to one or more aspects, it may be possible to obtain two index values that enable discrimination among a blood sample containing the DAC (hereinafter also referred to as a "DAC sample"), a blood sample containing the LA (hereinafter also referred to as an "LA sample"), and a blood sample deficient in a coagulation factor (hereinafter also referred to as a "coagulation factor deficient sample"). These index values make it possible to determine whether or not the blood sample of the subject is the DAC sample.

BRIEF DESCRIPTION OF DRAWINGS

FIG. 8 is a diagram illustrating an example of a screen that displays measurement results by a blood sample analyzer;

DETAILED DESCRIPTION

[1. Determination Method of Blood Sample]

Figure 1:
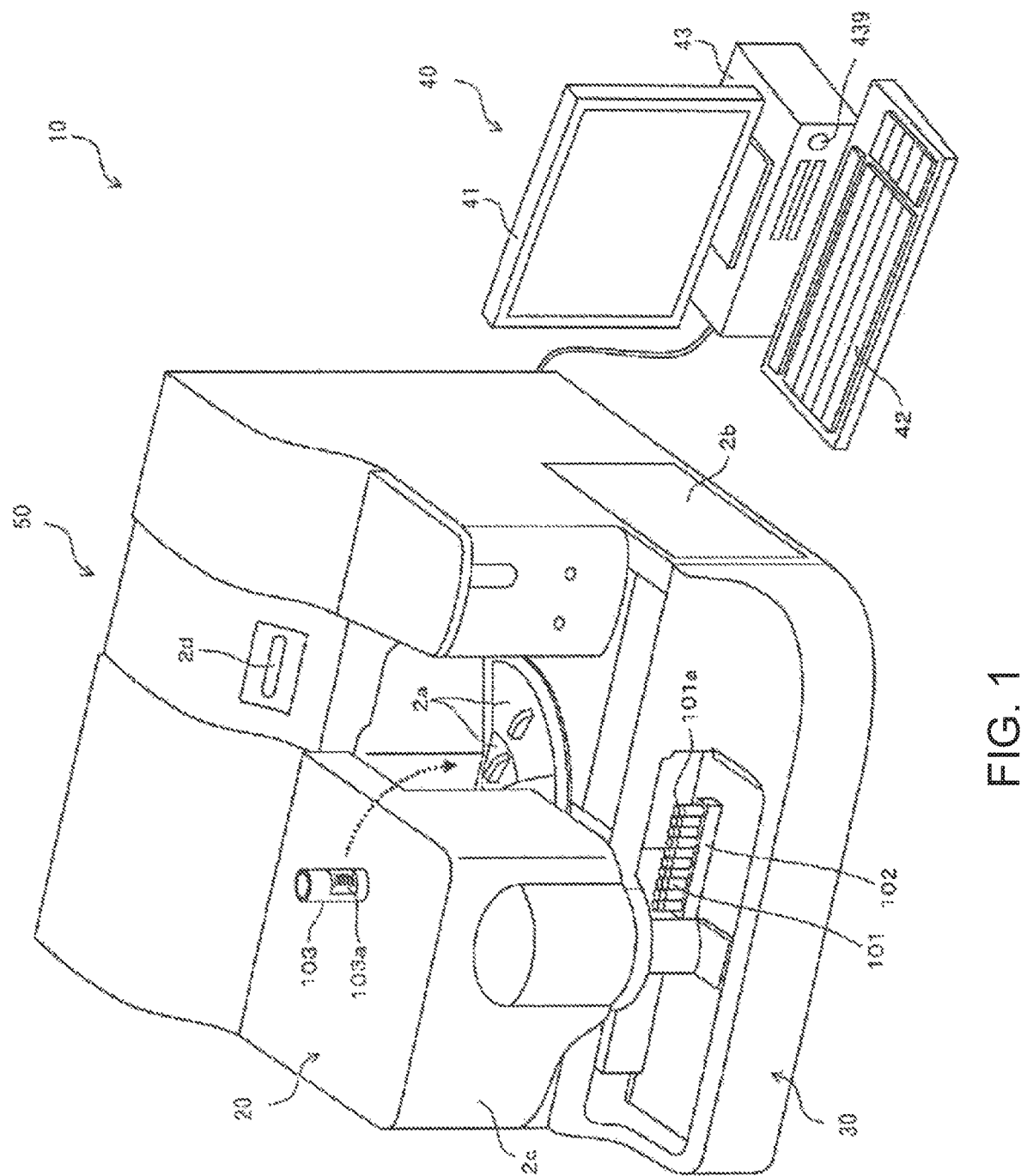
FIG. 1 is a perspective view illustrating an external configuration of a blood sample analyzer.

A determination method of a blood sample (hereinafter also referred to as the "determination method") of one or more embodiments is a method of determining whether or not a blood sample of a subject is a DAC sample. As described previously, the direct anticoagulant (DAC) is a drug that binds to a coagulation factor and directly inhibits the coagulation reaction mediated by the coagulation factor. The direct anticoagulant that is available for oral administration is called a direct oral anticoagulant (DOAC). A factor Xa inhibitor and a thrombin inhibitor are publicly known as the DAC in this technical field. The factor Xa inhibitor can directly bind to the factor Xa, thereby inhibiting transformation from prothrombin to thrombin. Examples of the factor Xa inhibitor include rivaroxaban, apixaban, edoxaban, betrixaban, otamixaban, razaxaban, darexaban, letaxaban, eribaxaban, antistasin, and the like. The thrombin inhibitor can directly bind to thrombin, thereby inhibiting fibrinogen activation mediated by thrombin. Examples of the thrombin inhibitor include dabigatran, bivalirudin, hirudin, lepirudin, desirudin, argatroban, melagatran, ximelagatran, and the like.

The determination method of one or more embodiments acquires each coagulation time of a blood sample of a subject, a normal blood sample, and a mixed sample obtained by mixing these samples. In this specification, an act of "acquiring coagulation time" means both actually measuring a coagulation time of a blood sample by use of a coagulation time measurement reagent and acquiring a value of a coagulation time of a blood sample measured and recorded in advance by use of a coagulation time measurement reagent.

In one or more embodiments, the coagulation time of the blood sample mentioned above represents the coagulation time measured by using each of first and second coagulation time measurement reagents. A first coagulation time measurement reagent is a coagulation time measurement reagent containing a phospholipid, while a second coagulation time measurement reagent is a coagulation time measurement reagent containing the phospholipid at a higher concentration than that of the first coagulation time measurement reagent. In the following, a coagulation time of the blood sample of the subject measured by using the first coagulation time measurement reagent is referred to as a "first coagulation time", a coagulation time of the normal blood sample measured by using the first coagulation time measurement reagent is referred to as a "second coagulation time", and a coagulation time of a mixed blood sample measured by using the first coagulation time measurement reagent is referred to as a "third coagulation time". Meanwhile, a coagulation time of the blood sample of the subject measured by using the second coagulation time measurement reagent is referred to as a "fourth coagulation time", a coagulation time of the normal blood sample measured by using the second coagulation time measurement reagent is referred to as a "fifth coagulation time", and a coagulation time of the mixed blood sample measured by using the second coagulation time measurement reagent is referred to as a "sixth coagulation time".

The blood sample of the subject may be either blood (whole blood) collected from the subject or plasma prepared by using this blood. Of these matters, the plasma is preferable and the plasma deprived of platelets is more preferable. The platelets can be removed by use of a publicly known method such as centrifugal separation and filter separation. In one or more embodiments, the blood sample of the subject is preferably a blood sample suspected to have a coagulation abnormality. Examples of the above-mentioned sample include a blood sample that manifests prolongation of a coagulation time in the course of an ordinary coagulation test, a blood sample collected from a patient with thrombosis or an individual suspected to have thrombosis, and the like.

The normal blood sample may be either blood (whole blood) collected from a normal individual or plasma prepared by using this blood. The normal plasma is preferable in one or more embodiments. The normal plasma may be either normal pooled plasma prepared by a medical institution and the like or commercially available normal plasma. Examples of the commercially available normal plasma include Control N (Sysmex Corporation), CRYOcheck Pooled Normal Plasma (Precision BioLogic Inc), and the like.

The mixed sample is a sample obtained by mixing the blood sample of the subject with the normal blood sample at least at one mixing ratio. The mixing ratio between the blood sample of the subject and the normal blood sample may be determined as appropriate. For example, at least one of 5, 10, 15, 20, 25, 30, 35, 40, 45, 50, 55, 60, 65, 70, 75, 80, 85, 90, and 95% (v/v) is selected as the ratio of the blood sample of the subject in the mixed sample. In one or more embodiments, it is preferable to prepare the mixed sample having the ratio of the blood sample of the subject equal to 50% (v/v). The preparation of the mixed sample may be conducted in accordance with a hand method or by using a fully automatic coagulation time measurement device.

The first and second coagulation time measurement reagents may be reagents for measuring coagulation time based on the publicly known measurement principle in this technical field. Examples of such reagents may include reagents for measuring at least one of dilute Russell's viper venom time (dRVVT), activated partial thromboplastin time (APTT), dilute activated partial thromboplastin time (dAPTT), prothrombin time (PT), dilute prothrombin time (dPT), thrombin time (TT), and dilute thrombin time (dTT). Among them, a dRVVT measurement reagent, a dAPTT measurement reagent, and an APTT measurement reagent are preferable. Meanwhile, commercially available coagulation time measurement reagents and reagent kits may be used. In one or more embodiments, it may be preferable that the first coagulation time measurement reagent and the second coagulation time measurement reagent are reagents for measuring the coagulation time based on the same measurement principle.

Examples of the phospholipid to be contained in the first and second coagulation time measurement reagents include phosphatidylethanolamine (PE), phosphatidylcholine (PC), and phosphatidylserine (PS). The first and second coagulation time measurement reagents contain one, or preferably two, or more preferably all kinds of the phospholipids selected from the group consisting of PE, PC, and PS. Each of the phospholipids may be a naturally occurring phospholipid or a synthetic phospholipid. From the viewpoint of improving sensitivity to the LA, a synthetic phospholipid or a naturally occurring phospholipid purified to 99% or above is preferable. While fatty acid side chains of PE, PC, and PS are not limited to particular side chains, examples thereof include palmitic acid, oleic acid, stearic acid, and the like. Among them, oleic acid is preferable.

The phospholipid concentration of the first coagulation time measurement reagent is not limited to a particular value as long as the concentration is lower than the phospholipid concentration of the second coagulation time measurement reagent. In one or more embodiments, the phospholipid concentration of the first coagulation time measurement reagent is preferably set to an adequate concentration for causing inhibition of the phospholipid by the LA (prolongation of the coagulation time) when the LA sample is measured. In this case, the first coagulation time measurement reagent corresponds to an LA screening reagent. To be more precise, when the blood sample and the first coagulation time measurement reagent are mixed at a volume ratio of 1:1, the concentration of the phospholipid in the reagent is in a range from 20 to 150 µg/mL or preferably in a range from 30 to 70 µg/mL, for example. If the mixing ratio between the blood sample and the first coagulation time measurement reagent is not 1:1, then the concentration of the phospholipid in the reagent may be appropriately adjusted in accordance with the mixing ratio.

The phospholipid concentration of the second coagulation time measurement reagent is not limited to a particular value as long as the concentration is higher than the phospholipid concentration of the first coagulation time measurement reagent. In one or more embodiments, the phospholipid concentration of the second coagulation time measurement reagent is preferably set to an adequate concentration with which it is possible to suppress or reduce the inhibition of the phospholipid by the LA (the prolongation of the coagulation time) when the LA sample is measured. In this case, the second coagulation time measurement reagent corresponds to an LA confirmation test reagent. For example, the phospholipid concentration of the second coagulation time measurement reagent may be not less than 1.1 times and not more than 100 times as high as the phospholipid concentration of the first coagulation time measurement reagent. To be more precise, when the blood sample and the second coagulation time measurement reagent are mixed at a volume ratio of 1:1, the concentration of the phospholipid in the reagent is in a range from 150 to 2000 µg/mL or preferably in a range from 150 to 600 µg/mL, for example. If the mixing ratio between the blood sample and the second coagulation time measurement reagent is not 1:1, then the concentration of the phospholipid in the reagent may be appropriately adjusted in accordance with the mixing ratio.

The first and second coagulation time measurement reagents contain a component required for coagulation depending on the type of the coagulation time to be measured. In this specification, the component required for coagulation means a component required for triggering in-vitro blood coagulation. Such a component has been publicly known in this technical field, and examples of the component include an activator, snake venom, a tissue factor, and the like. The activator is preferably a contact factor activator and examples thereof include ellagic acid, kaolin, celite, silica, and the like. Such ellagic acid may be ellagic acid in the state of a chelate formed with a metal ion. Examples of the snake venom include Russell's viper venom, textarin snake venom, ecarin snake venom, and the like. Examples of the tissue factor include a tissue factor derived from rabbit brain or human placenta, a recombinant tissue factor, and the like. In one or more embodiments, it may be preferable that the first coagulation time measurement reagent and the second coagulation time measurement reagent contain the same component.

The first and second coagulation time measurement reagents may contain calcium ions for triggering the blood coagulation. In this case, each of the first and second coagulation time measurement reagents may be a single liquid reagent containing the phospholipid, the component required for coagulation, and calcium ions. Alternatively, the first coagulation time measurement reagent may be a two-liquid reagent formed from a first partial reagent containing the phospholipid and the component required for coagulation and a second partial reagent containing calcium ions. Likewise, the second coagulation time measurement reagent may be a two-liquid reagent formed from a third partial reagent containing the phospholipid and the component required for coagulation and a fourth partial reagent containing calcium ions. In one or more embodiments, a single partial reagent containing calcium ions may be used as the second partial reagent in the first coagulation time measurement reagent and as the fourth partial reagent in the second coagulation time measurement reagent.

The calcium ions are preferably supplied into the coagulation time measurement reagents in the form of a calcium salt or an aqueous solution thereof. Examples of the calcium salt include calcium chloride and the like. The content of calcium ions in each of the first and second coagulation time measurement reagents may be in an adequate amount for causing coagulation, and such an amount is usually in a range of not less than 2 mmol/L and not more than 40 mmol/L or preferably in a range of not less than 4 mmol/L and not more than 30 mmol/L expressed in the concentration of calcium chloride, for example. When any of the coagulation time measurement reagents is the two-liquid reagent, the partial reagent containing calcium ions is preferably an aqueous solution of calcium chloride. Note that the unit "mmol/L" may also be expressed as "mM" in this specification.

If the first and second coagulation time measurement reagents are the reagents that contain the Russell's viper venom as the component required for coagulation, these reagents do not have to contain calcium ions because the Russell's viper venom induces the blood coagulation by directly activating the factor X.

As described above, the blood coagulation by the Russell's viper venom is induced by direct activation of the factor X and is not mediated by a factor VII and a contact factor in an extrinsic coagulation pathway or a factor VIII in an intrinsic coagulation pathway. For this reason, the dRVVT has been known to have high sensitivity to the LA without being affected by contact factor abnormality, a factor VIII deficiency, and the like. In one or more embodiments, the first coagulation time measurement reagent is preferably a reagent (a dRVVT measurement reagent) that contains the Russell's viper venom, and the phospholipid while the second coagulation time measurement reagent is preferably a reagent that contains the Russell's viper venom, and the phospholipid at a higher concentration than that in the first coagulation time measurement reagent.

In one or more embodiments, it is preferable to acquire the first to sixth coagulation times by actually measuring these coagulation times by use of the first and second coagulation time measurement reagents. The measurement of each coagulation time is performed on a measurement specimen prepared by mixing each of the aforementioned blood samples with the first or second coagulation time measurement reagent. Specifically, the first coagulation time is acquired by measuring a first measurement specimen obtained by mixing the blood sample of the subject with the first coagulation time measurement reagent, the second coagulation time is acquired by measuring a second measurement specimen obtained by mixing the normal blood sample with the first coagulation time measurement reagent, and the third coagulation time is acquired by measuring a third measurement specimen obtained by mixing the mixed sample with the first coagulation time measurement reagent. Meanwhile, the fourth coagulation time is acquired by measuring a fourth measurement specimen obtained by mixing the blood sample of the subject with the second coagulation time measurement reagent, the fifth coagulation time is acquired by measuring a fifth measurement specimen obtained by mixing the normal blood sample with the second coagulation time measurement reagent, and the sixth coagulation time is acquired by measuring a sixth measurement specimen obtained by mixing the mixed sample with the second coagulation time measurement reagent.

Reaction conditions of each blood sample and each coagulation time measurement reagent can be appropriately determined based on the type of the reagent. For example, when the first or second coagulation time measurement reagent is the two-liquid reagent, a reaction time period between the blood sample and the first or third partial reagent is usually set not less than 1 minute and not more than 10 minutes or preferably not less than 3 minutes and not more than 5 minutes. A temperature condition is usually set not less than 25° C. and not more than 45° C. or preferably not less than 35° C. and not more than 38° C. The preparation of the measurement specimens may be conducted in accordance with a hand method or by using a fully automatic measurement device. Examples of such a device include CS-5100 (Sysmex Corporation), CS-2400 (Sysmex Corporation), CS-2000i (Sysmex Corporation), and the like.

The measurement of the coagulation time is to be carried out promptly after the preparation of the measurement specimen. To be more precise, when the first or second coagulation time measurement reagent is the two-liquid reagent, the measurement of the coagulation time is to be started at a point of time when the second or fourth partial reagent containing calcium ions is added to the mixture of the blood sample and the first or third partial reagent. When the first or second coagulation time measurement reagent is the single liquid reagent containing calcium ions or the snake venom, the measurement of the coagulation time is to be started at a point of time when the reagent is added to the blood sample.

The measurement of the coagulation time may be conducted in accordance with a hand method or by using the above-mentioned fully automatic coagulation time measurement device. The measurement is preferably conducted by using the fully automatic coagulation time measurement device. When the coagulation time is measured by using this device, the measurement specimen is irradiated with light and the coagulation time is calculated based on optical information thus obtained. The light used for irradiation may be light that is usually employed for the measurement of the coagulation time. An example of such light includes the light having the wavelength near 660 nm. Though such a light source is not limited, examples of the light source include a light-emitting diode, a halogen lamp, and the like. As the measurement specimen is irradiated with the light from the light source, the measurement specimen causes scattered light and transmitted light. In one or more embodiments, the optical information concerning an amount of light includes information concerning an amount of scattered light and an amount of transmitted light, for example. Among them, scattered light intensity, transmittance, absorbance, and the like are preferable.

In one or more embodiments, the first to sixth coagulation times may be measured simultaneously or measured sequentially. When the first to sixth coagulation times are measured sequentially, the order of the measurement is not limited.

In one or more embodiments, the second coagulation time may be a predetermined coagulation time with the first coagulation time measurement reagent. Meanwhile, the fifth coagulation time may be a predetermined coagulation time with the second coagulation time measurement reagent. In other words, coagulation time of the normal blood sample measured and recorded in advance by using the first coagulation time measurement reagent may be used as the second coagulation time, and coagulation time of the normal blood sample measured and recorded in advance by using the second coagulation time measurement reagent may be used as the fifth coagulation time. In this way, it is possible to curtail the preparation and measurement of the second and fifth measurement specimens. If the first and second coagulation time measurement reagents come from commercially available reagents or reagent kit, then coagulation time described in an instruction attached thereto may be used as the second and fifth coagulation times.

Hence, in one or more embodiments, the first coagulation time is acquired by measuring the first measurement specimen obtained by mixing the blood sample of the subject with the first coagulation time measurement reagent, the second coagulation time is the predetermined coagulation time of the normal blood sample with the first coagulation time measurement reagent, and the third coagulation time is acquired by measuring the third measurement specimen obtained by mixing the mixed sample with the first coagulation time measurement reagent. Meanwhile, the fourth coagulation time is acquired by measuring the fourth measurement specimen obtained by mixing the blood sample of the subject with the second coagulation time measurement reagent, the fifth coagulation time is the predetermined coagulation time of the normal blood sample with the second coagulation time measurement reagent, and the sixth coagulation time is acquired by measuring the sixth measurement specimen obtained by mixing the mixed sample with the second coagulation time measurement reagent. These one or more embodiments are substantially the same as the above-described one or more embodiments except that the coagulation times of the normal blood sample measured and recorded in advance are used as the second and fifth coagulation times.

In the determination method of one or more embodiments, a first index value is acquired based on the first coagulation time, the second coagulation time, and the third coagulation time. A second index value is acquired based on the fourth coagulation time, the fifth coagulation time, and the sixth coagulation time. In one or more embodiments, the first and second index values are preferably values for quantitatively evaluating results of the mixing test based on the coagulation times of the blood sample of the subject, the normal blood sample, and the mixed sample thereof.

In the LA test, it is recommended to acquire the index values such as the ICA for quantitatively evaluating the results of the mixing test from the coagulation times measured by use of a screening reagent with a low phospholipid concentration. On the other hand, acquisition of an index value from coagulation times measured by using a confirmation test reagent with a high phospholipid concentration is not carried out in this technical field. This is because the reagent with the high phospholipid concentration suppresses the prolongation of the coagulation time due to the LA, and useful information cannot be obtained from an acquired index value. However, the inventor of this application has attempted to acquire two types of index values by measuring the coagulation times of the plasma of the subject, the normal plasma, and the mixed plasma while using two types of coagulation time measurement reagents with different phospholipid concentrations. As a consequence, the inventor has found out that a DAC sample, an LA sample, and a coagulation factor deficient sample can be discriminated from one another by using the two types of index values.

In one or more embodiments, the first and second index values may be values obtained by the same calculation method or values obtained by different calculation methods. Preferably, the first and second index values are the values obtained by the same calculation method. For example, the first index value may be a value derived from the a difference between the second coagulation time and the third coagulation time and from the first coagulation time, while the second index value may be a value derived from a difference between the fifth coagulation time and the sixth coagulation time and from the fourth coagulation time.

The difference between the second coagulation time and the third coagulation time is calculated by any one of the following formulae, namely, (the difference between the second coagulation time and the third coagulation time)=(the second coagulation time)−(the third coagulation time), and (the difference between the second coagulation time and the third coagulation time)=(the third coagulation time)−(the second coagulation time).

Likewise, the difference between the fifth coagulation time and the sixth coagulation time is calculated by any one of the following formulae, namely, (the difference between the fifth coagulation time and the sixth coagulation time)=(the fifth coagulation time)−(the sixth coagulation time), and (the difference between the fifth coagulation time and the sixth coagulation time)=(the sixth coagulation time)−(the fifth coagulation time).

In one or more embodiments a value derived from multiplication of the value calculated by any of the aforementioned formulae by a constant may be acquired as the corresponding difference.

Examples of the value derived from the difference between the second coagulation time and the third coagulation time and from the first coagulation time include a product of or a ratio between the value of the difference and the value of the first coagulation time. Likewise, examples of the value derived from the difference between the fifth coagulation time and the sixth coagulation time and from the fourth coagulation time include a product of or a ratio between the value of the difference and the value of the fourth coagulation time.

In one or more embodiments, it may be preferable that the first index value is a value related to the ratio of the difference between the second coagulation time and the third coagulation time to the value of the first coagulation time, and the second index value is a value related to the ratio of the difference between the fifth coagulation time and the sixth coagulation time to the value of the fourth coagulation time. These values related to the ratios include not only the values of the ratios but also values derived from the values of the ratios.

The value of the ratio as the first index value is a value calculated by any of the following formulae, namely, (the value of the ratio)=(the difference between the second coagulation time and the third coagulation time)/(the first coagulation time), and (the value of the ratio)=(the first coagulation time)/(the difference between the second coagulation time and the third coagulation time).

Likewise, the value of the ratio as the second index value is a value calculated by any of the following formulae, namely, (the value of the ratio)=(the difference between the fifth coagulation time and the sixth coagulation time)/(the fourth coagulation time), and (the value of the ratio)=(the fourth coagulation time)/(the difference between the fifth coagulation time and the sixth coagulation time).

Examples of the value derived from the value of the ratio include: a value obtained by multiplying the value of the ratio by a constant; a value obtained by adding a constant to the value of the ratio; a value obtained by subtracting a constant from the value of the ratio; the reciprocal of the value of the ratio; a value obtained by a combination of any of these calculations; and the like.

In one or more embodiments, the first index value is preferably the value of the ratio acquired by the following formula (1), and the second index value is preferably the value of the ratio acquired by the following formula (2), namely: (the first index value)=[(the third coagulation time)−(the second coagulation time)]/(the first coagulation time) . . . formula (1); and (the second index value)=[(the sixth coagulation time)−(the fifth coagulation time)]/(the fourth coagulation time) . . . formula (2).

In one or more embodiments, ratios (%) obtained by multiplying the values calculated in accordance with the formulae (1) and (2) mentioned above by 100 may be acquired as the first and second index values. In this case, the obtained ratios correspond to the ICA to be described later.

In one or more embodiments, a publicly known quantification index may be used as each of the first and second index values. Examples of the publicly known quantification index include the ICA, Percent Correction (PC), and the like. Note that the ICA itself has been disclosed in Pengo V. et al., Update of the guidelines for lupus anticoagulant detection, Journal of Thrombosis and Haemostasis 2009; 7: 1737-1740, while the PC itself has been disclosed in Chang S-H. et al., "Percent Correction" Formula for Evaluation of Mixing Studies, Am J Clin Pathol 2002; 117: 62-73. Now, the ICA and the PC are described below.

The ICA is an index used for determination of an LA sample and is also called a Rosner Index. The ICA is calculated by the following formula.

ICA=[(E−B)/A]×100 (in which, A: the coagulation time of the plasma of the subject, B: the coagulation time of the normal plasma, and E: the coagulation time of the mixed plasma in which the ratio of the plasma of the subject is 50% (v/v)).

The PC applies different formulae for computation as cited below depending on the ratio of the plasma of the subject in the mixed sample.

PC (9:1)=[(A−C)/(A−B)]×100, PC (8:2)=[(A−D)/(A−B)]×100, PC (5:5)=[(A−E)/(A−B)]×100, PC (2:8)=[(A−F)/(A−B)]×100, PC (1:9)=[(A−G)/(A−B)]×100 (in which, A: the coagulation time of the plasma of the subject, B: the coagulation time of the normal plasma, C: the coagulation time of the mixed plasma in which the ratio of the plasma of the subject is 10% (v/v); D: the coagulation time of the mixed plasma in which the ratio of the plasma of the subject is 20% (v/v); E: the coagulation time of the mixed plasma in which the ratio of the plasma of the subject is 50% (v/v); F:

the coagulation time of the mixed plasma in which the ratio of the plasma of the subject is 80% (v/v); and G: the coagulation time of the mixed plasma in which the ratio of the plasma of the subject is 90% (v/v)).

The method of one or more embodiments performs the determination based on the first index value and the second index value as to whether or not the blood sample of the subject is a blood sample that contains the DAC. In one or more embodiments, it may be preferable that the first index value is compared with a first threshold and the second index value is compared with a second threshold, and then the determination is made based on results of the comparison. The first threshold and the second threshold may be the same value or different values. When the first and second index values are the values obtained by the same calculation method, the first threshold and the second threshold are preferably the same value.

For example, the first index values of the DAC sample and the LA sample calculated by using the formula (1) tend to be higher than that of the coagulation factor deficient sample. Meanwhile, the second index value of the DAC sample calculated by using the formula (2) tends to be higher than those of the LA sample and the coagulation factor deficient sample. Accordingly, when the first index value is higher than the first threshold and the second index value is higher than the second threshold, the blood sample of the subject can be determined as the blood sample containing the DAC. Meanwhile, when the first index value is lower than the first threshold or when the second index value is lower than the second threshold, the blood sample of the subject can be determined as the blood sample with a cause of coagulation abnormality other than the DAC. Examples of the cause of coagulation abnormality other than the DAC include the LA and the coagulation factor deficiency.

In one or more embodiments, when the blood sample of the subject is determined as the blood sample with the cause of coagulation abnormality other than the DAC, it is also possible to determine whether the blood sample of the subject is the blood sample containing the LA or the blood sample deficient in the coagulation factor based on the first and second index values. Procedures of the determination when the first and second index values are the values calculated by the formulae (1) and (2), respectively, are discussed as an example. If the first index value is equal to or above the first threshold and the second index value is below the second threshold, then the blood sample of the subject may be determined as the blood sample containing the LA. Meanwhile, if the first index value is below the first threshold and the second index value is below the second threshold, then the blood sample of the subject may be determined as the blood sample deficient in the coagulation factor. Here, if the first index value is below the first threshold and the second index value is equal to or above the second threshold, then the blood sample of the subject may be determined to have a cause of coagulation abnormality other than the DAC, the LA, or the coagulation factor deficiency.

In one or more embodiments, the numerical values of the first threshold and the second threshold per se are not limited. For example, the first and second thresholds can be empirically set by accumulation of data on the coagulation time of blood samples of patients dosed with the DAC, LA-positive patients, and patients with coagulation factor deficiencies. Alternatively, the first index value and the second index value can be acquired from a group of blood samples of patients dosed with the DAC, a group of blood samples of LA-positive patients, and a group of blood samples of patients with coagulation factor deficiencies, respectively, and values that can clearly discriminate these groups from one another can be set as the first and second thresholds based on the acquired values. A statistical method such as an ROC analysis may be used for calculation of the thresholds.

[2. Blood Sample Analyzer and Computer Program]

An example of a blood sample analyzer of one or more embodiments is described below with reference to the drawings. It is to be noted, however, that one or more embodiments is not limited only to the following example. The blood sample analyzer may also be hereinafter simply referred to as the "analyzer". As illustrated in FIG. 1, a blood sample analyzer 10 includes a measurement device 50 that performs preparation and optical measurement of a measurement specimen, and a control device 40 that analyzes measurement data acquired by the measurement device 50 and gives instructions to the measurement device 50. The measurement device 50 includes a measurement part 20 that acquires optical information concerning an amount of light from the measurement specimen, and a sample transporter 30 located in front of the measurement part 20.

In one or more embodiments, the measurement part 20 and the sample transporter 30 are integrated with each other to constitute part of the analyzer 10. In one or more embodiments, the sample transporter 30 may be provided separately from the analyzer 10. For example, a large-scale system including two or more analyzers may adopt a configuration in which the analyzers are connected to a large transport line instead of providing each analyzer with the sample transporter.

The measurement part 20 is provided with lids 2a and 2b, a cover 2c, and a power button 2d. A user can open the lid 2a to replace a reagent container 103 installed on reagent tables 11 and 12 (see FIG. 2) with a new reagent container 103, or to newly add another reagent container 103. A barcode label 103a printed with a type of a contained reagent as well as a barcode including a reagent ID formed from a serial number for the reagent is attached to the reagent container 103.

Figure 2:
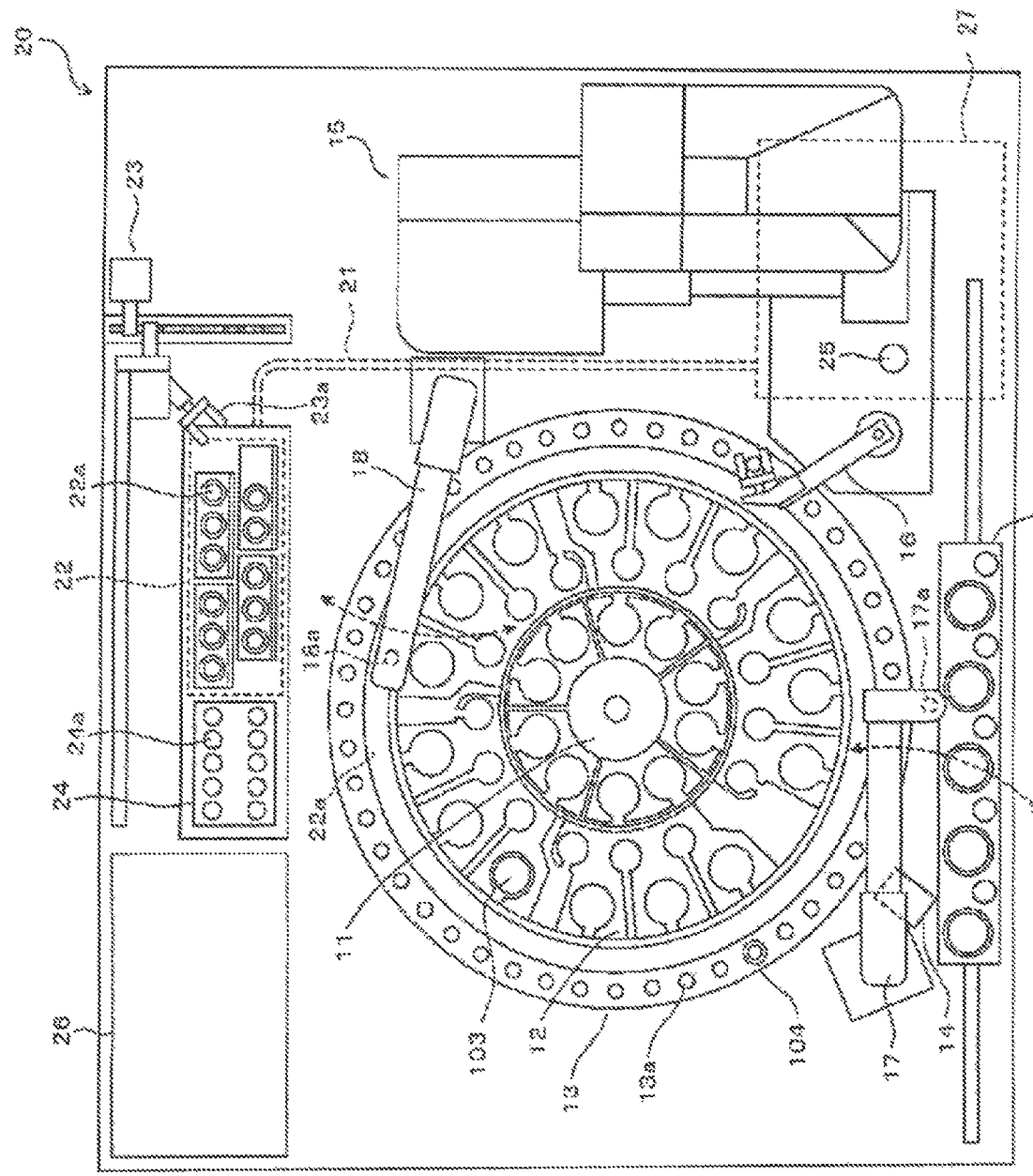
FIG. 2 is a plan view illustrating an inside of a measurement part of a blood sample analyzer viewed from above.

The user can open the lid 2b to replace a lamp unit 27 (see FIG. 2). Meanwhile, the user can open the cover 2c to replace a piercer 17a (see FIG. 2). The sample transporter 30 transports sample containers 101 supported by a sample rack 102 to a position of aspiration by the piercer 17a. Each sample container 101 is tightly sealed with a cap 101a made of rubber.

When using the blood sample analyzer 10, the user first starts the measurement part 20 by pressing the power button 2d of the measurement part 20, and starts the control device 40 by pressing a power button 439 of the control device 40. When the control device 40 is started, a log-on screen is displayed on a display part 41 or a display. The user logs on the control device 40 by inputting a user name and a password on the log-on screen, and thus starts using the blood sample analyzer 10.

A configuration of the measurement device 50 is described. As illustrated in FIG. 2, the measurement part 20 includes the reagent tables 11 and 12, a cuvette table 13, a barcode reader 14, a cuvette supply part 15, a catcher 16, a sample dispensing arm 17, a reagent dispensing arm 18, a time-critical sample setting part 19, an optical fiber 21, a detection part 22, a cuvette transfer part 23, a heater 24, a disposal port 25, a fluid part 26, and the lamp unit 27. In one or more embodiments, the measurement part 20 has a function as a measurement specimen preparation part to prepare a measurement specimen from a blood sample and a function as an optical information acquisition part to acquire optical information from the prepared measurement specimen.

(Measurement Specimen Preparation Part)

The reagent tables 11 and 12 as well as the cuvette table 13 have an annular shape and are rendered rotatable, respectively. The reagent tables 11 and 12 correspond to reagent storage parts and the reagent containers 103 are placed thereon. The barcodes on the reagent containers 103 placed on the reagent tables 11 and 12 are read out with the barcode reader 14. The information (the types of the reagents and the reagent IDs) read out of the barcodes is inputted to the control device 40 and stored in a hard disk 434 (see FIG. 6).

In the device of one or more embodiments, the reagent containers 103 which contain the first partial reagent and the second partial reagent (the calcium chloride aqueous solution) of the first coagulation time measurement reagent, the third partial reagent and the fourth partial reagent (the calcium chloride aqueous solution) of the second coagulation time measurement reagent, and the like, respectively, are placed on the reagent table 11 and/or the reagent table 12. In this example, each of the first and second coagulation time measurement reagents is the two-liquid reagent. However, any of these reagents may be the single liquid reagent instead.

A support part 13a formed from holes that can support cuvettes 104 is formed in the cuvette table 13. The new cuvettes 104 put in the cuvette supply part 15 by the user are sequentially transferred by the cuvette supply part 15 and are set on the support part 13a in the cuvette table 13 by the catcher 16.

A stepping motor is connected to each of the sample dispensing arm 17 and the reagent dispensing arm 18 so that the arms can perform vertical movement and rotational movement. The piercer 17a with a tip formed sharp so as to be able to pierce the cap 101a of each sample container 101 is installed at a leading end of the sample dispensing arm 17. A pipette 18a is installed at a leading end of the reagent dispensing arm 18. A tip of the pipette 18a is formed flat unlike the piercer 17a. Moreover, a capacitive fluid level detection sensor 213 (see FIG. 3) is connected to the pipette 18a.

When the sample container 101 is transported to a predetermined position by the sample transporter 30 (see FIG. 1), the piercer 17a is located immediately above the sample container 101 by the rotational movement of the sample dispensing arm 17. Then, the sample dispensing arm 17 is moved downward and the piercer 17a penetrates the cap 101a of the sample container 101, whereby the blood sample contained in the sample container 101 is aspirated by the piercer 17a. When a time-critical blood sample is set in the time-critical sample setting part 19, the piercer 17a suspends the treatment of the sample supplied from the sample transporter 30 and aspirates the time-critical blood sample. The blood sample aspirated by the piercer 17a is ejected onto an empty cuvette 104 on the cuvette table 13.

The cuvette 104 on which the blood sample is ejected is transferred from the support part 13a of the cuvette table 13 to a support part 24a of the heater 24 by using a catcher 23a of the cuvette transfer part 23. The heater 24 heats the blood sample contained in the cuvette 104 placed in the support part 24a at a predetermined temperature (such as 37° C.) for a predetermined period of time. When the heating of the blood sample by the heater 24 is completed, this cuvette 104 is grasped again by the catcher 23a. Then, this cuvette 104 is located at a predetermined position while being grasped by the catcher 23a, and the reagent aspirated by the pipette 18a is ejected into the cuvette 104.

At the dispensation of the reagent by the pipette 18a, the reagent tables 11 and 12 are rotated first and the reagent container 103 containing the reagent corresponding to a measurement item is transported to a position of aspiration by the pipette 18a. Then, a position in the vertical direction of the pipette 18a is located at a position of the origin based on a sensor for detecting the position of the origin, and then the pipette 18a is moved down by using the fluid level detection sensor 213 until a lower end of the pipette 18a comes into contact with a fluid level of the reagent. When the lower end of the pipette 18a comes into contact with the fluid level of the reagent, the pipette 18a is moved further downward so that the pipette 18a can aspirate a required amount of the reagent. Then, the downward movement of the pipette 18a is stopped and the reagent is aspirated by the pipette 18a. The reagent aspirated by the pipette 18a is ejected into the cuvette 104 grasped by the catcher 23a. Then, the blood sample and the reagent in the cuvette 104 are agitated by a vibrating function of the catcher 23a. Thus, the measurement specimen is prepared. Thereafter, the cuvette 104 containing the measurement specimen is transferred by the catcher 23a to a support part 22a of the detection part 22.

(Optical Information Acquisition Part)

Figure 4:
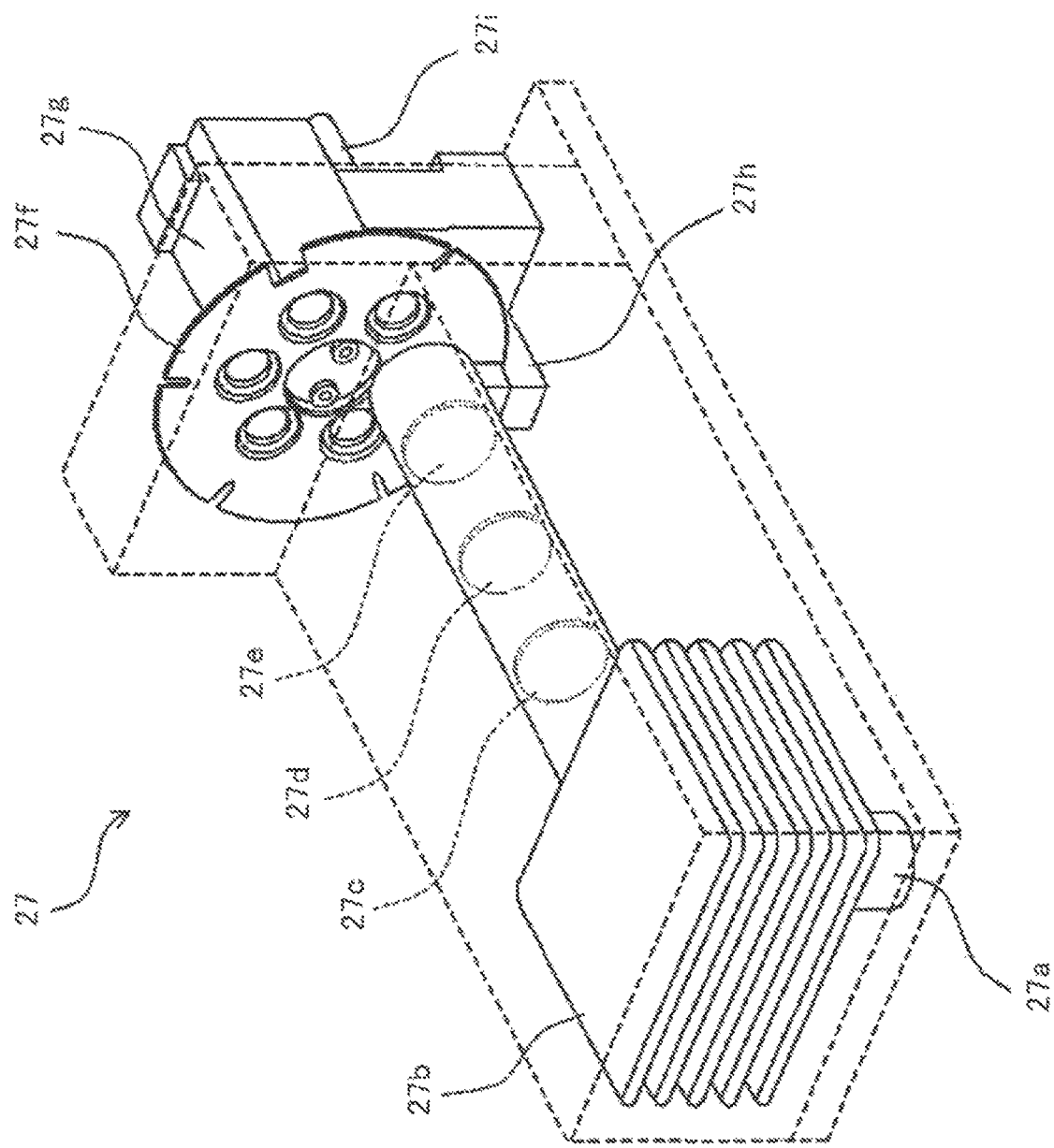
FIG. 4 is a diagram illustrating a configuration of a lamp unit provided in a measurement device.

The lamp unit 27 emits light of multiple wavelength types used for detection of optical signals by the detection part 22. An example of a configuration of the lamp unit 27 is described with reference to FIG. 4. The lamp unit 27 corresponds to a light source, which includes a halogen lamp 27a, a lamp case 27b, condenser lenses 27c to 27e, and a filter part 27f in a disc shape, a motor 27g, a light transmissive sensor 27h, and an optical fiber coupler 27i.

With reference to FIG. 2, light from the lamp unit 27 is supplied to the detection part 22 through the optical fiber 21. The detection part 22 is provided with support parts 22a each in the shape of a hole. A cuvette 104 can be inserted into each of the support parts 22a. End portions of the optical fiber 21 are attached to the support parts 22a, respectively, so that the cuvette 104 supported by each support part 22a can be irradiated with the light from the optical fiber 21. The detection part 22 irradiates the cuvette 104 with the light supplied from the lamp unit 27 through the optical fiber 21, and detects an amount of the light transmitted through the cuvette 104 (or the scattered light from the cuvette 104).

Figure 5A:
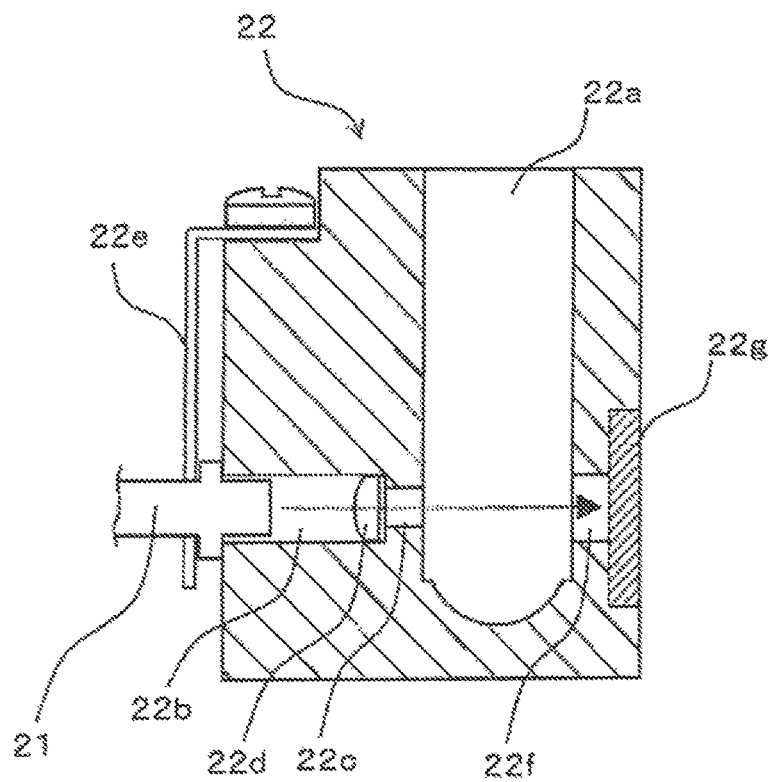
FIG. 5A is a diagram illustrating a configuration of a detection part provided in a measurement device.

A configuration example of one of the support parts 22a arranged in the detection part 22 is illustrated with reference to FIGS. 5A to 5D. Note that other support parts 22a have the same configuration. With reference to FIG. 5A, a circular hole 22b into which a tip end of the optical fiber 21 is inserted is formed in the detection part 22. Moreover, a circular communication hole 22c to establish communication between the hole 22b with the support part 22a is formed in the detection part 22. A diameter of the hole 22b is larger than a diameter of the communication hole 22c. A lens 22d to condense the light from the optical fiber 21 is located at an end portion of the hole 22b. Furthermore, a hole 22f is formed in an inner wall surface of the support part 22a at a position opposed to the communication hole 22c. A light detector 22g is located at the back of this hole 22f. The light detector 22g corresponds to a light receiving part and outputs an electric signal corresponding to an amount of received light. The light passed through the lens 22d is condensed on a light receiving surface of the light detector 22g through the communication hole 22c, the support part 22a, and the hole 22f. An end of the optical fiber 21 is kept from falling off by a plate spring 22e while maintaining the state of insertion into the hole 22b.

Figure 5B:
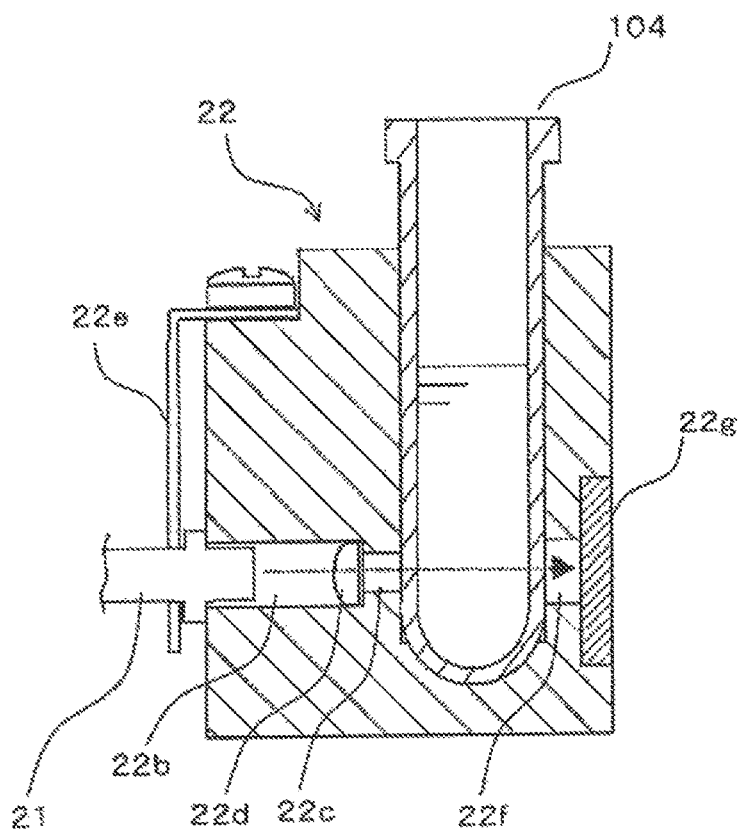
FIG. 5B is a diagram illustrating a configuration of a detection part provided in a measurement device.

With reference to FIG. 5B, when the cuvette 104 is supported by the support part 22a, the light condensed by the lens 22d is passed through the cuvette 104 and the specimen contained in the cuvette 104 and is made incident on the light detector 22g. Turbidity of the specimen is increased as the blood coagulation reaction of the specimen progresses. Along with this increase, the amount of light transmitted through the specimen (an amount of transmitted light) is decreased and a level of a detection signal of the light detector 22g is reduced.

Figure 5C:
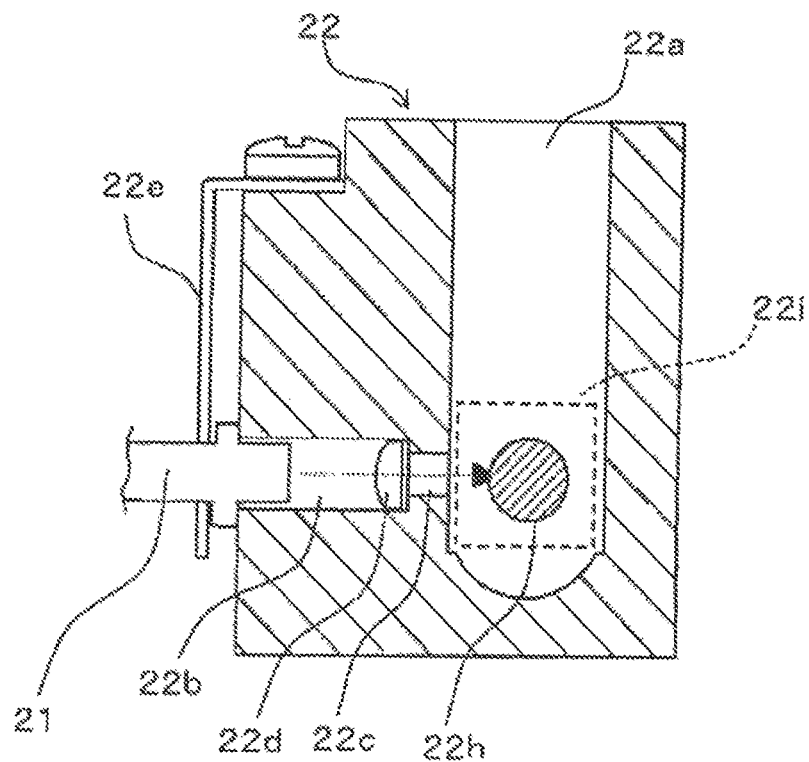
FIG. 5C is a diagram illustrating a configuration of a detection part provided in a measurement device.
Figure 5D:
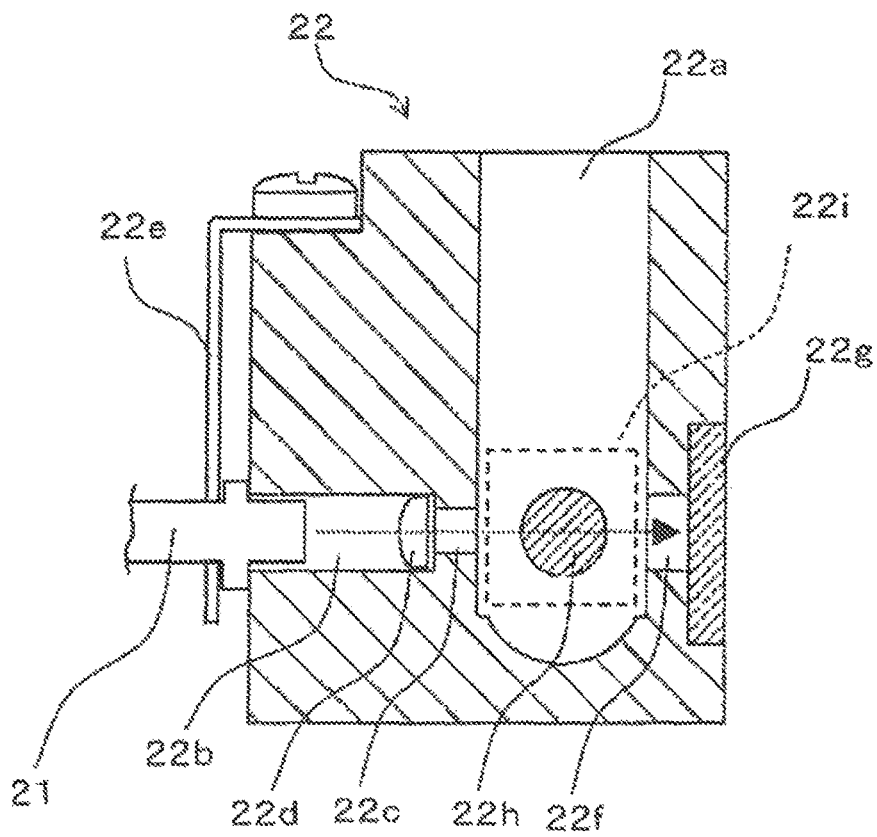
FIG. 5D is a diagram illustrating a configuration of a detection part provided in a measurement device.

A configuration of the detection part 22 in the case of using the scattered light is described with reference to FIG. 5C. A hole 22h is provided in an inner side surface of the support part 22a at the same height position as that of the communication hole 22c. A light detector 22i is located at the back of this hole 22h. When the cuvette 104 is inserted into the support part 22a and the light is emitted from the optical fiber 21, the light scattered by the measurement specimen in the cuvette 104 is projected onto the light detector 22i through the hole 22h. In this example, a detection signal from the light detector 22i indicates intensity of the scattered light from the measurement specimen. Meanwhile, both the transmitted light transmitted through the measurement specimen and the scattered light scattered by the measurement specimen may be detected as illustrated in FIG. 5D.

As described above, the detection part 22 irradiates the cuvette 104 with the light supplied from the lamp unit 27 and acquires the optical information from the measurement specimen. The optical information thus acquired is transmitted to the control device 40. The control device 40 performs an analysis based on the optical information and displays a result of analysis on the display part 41.

After the completion of the measurement, the cuvette 104 which is no longer necessary is transported by the cuvette table 13 and discarded to the disposal port 25 by the catcher 16. Note that the piercer 17a and the pipette 18a are cleaned as needed by a liquid such as a cleaning fluid supplied from the fluid part 26 in the course of the measurement operation.

Figure 3:
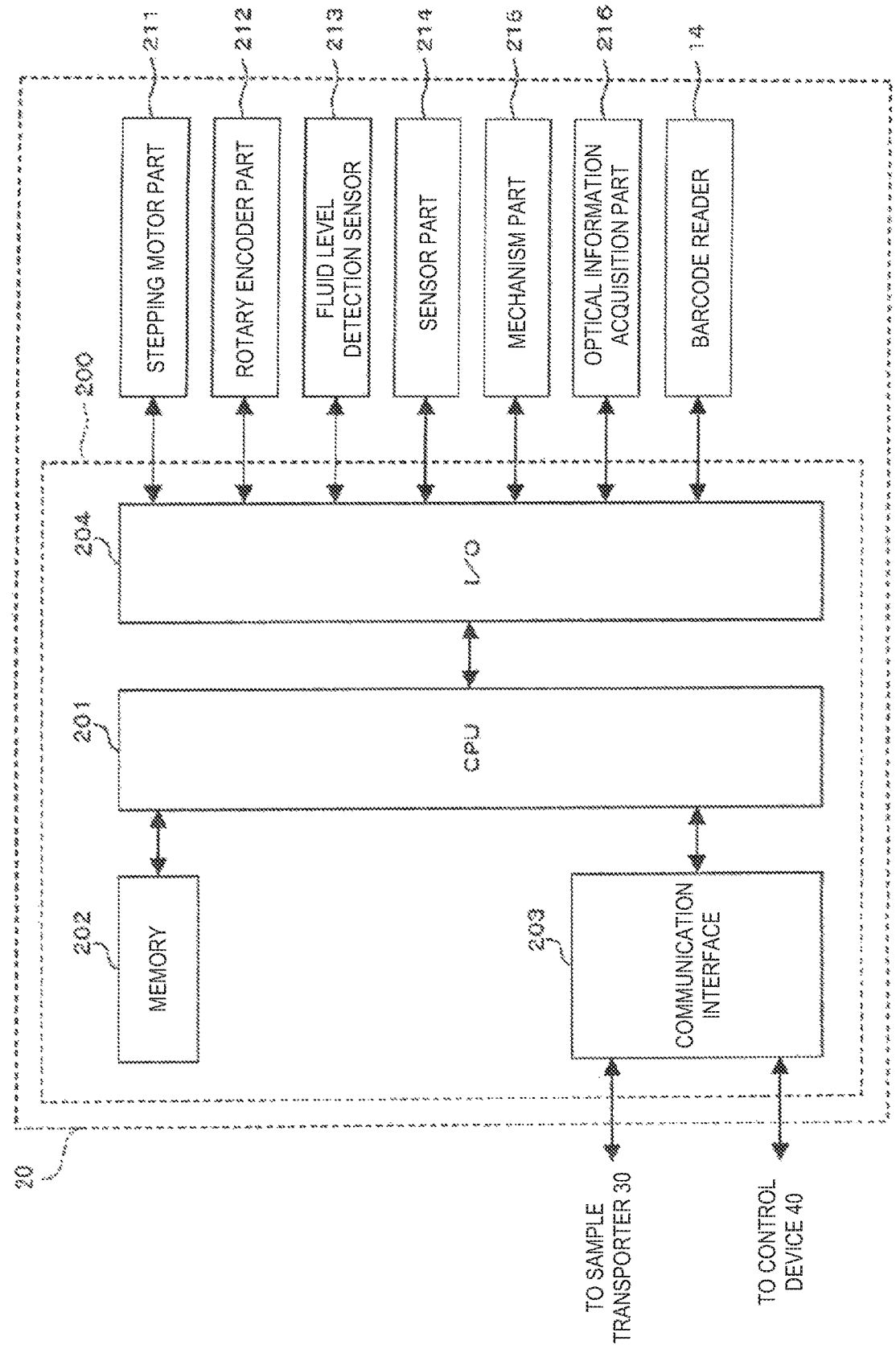
FIG. 3 is a diagram illustrating a configuration of a measurement part of a blood sample analyzer.

A description is given of a hardware configuration of the measurement device 50. As illustrated in FIG. 3, the measurement part 20 includes a control part 200, a stepping motor part 211, a rotary encoder part 212, the fluid level detection sensor 213, a sensor part 214, a mechanism part 215, an optical information acquisition part 216, and the barcode reader 14. The control part 200 has a function to control operations of the respective mechanisms in the measurement part 20 and the sample transporter 30.

With reference to FIG. 3, the control part 200 includes a CPU 201, a memory 202, a communication interface 203, and an I/O interface 204. The CPU 201 executes programs stored in the memory 202. The memory 202 is formed from a ROM, a RAM, a hard disk, and the like. Meanwhile, the CPU 201 drives the sample transporter 30 and performs transmission and reception of instruction signals and data to and from the control device 40 through the communication interface 203. Moreover, the CPU 201 controls respective parts in the measurement part 20 and receives signals outputted from the respective parts through the I/O interface 204.

The stepping motor part 211 includes stepping motors provided for driving the reagent tables 11 and 12, the cuvette table 13, the catcher 16, the sample dispensing arm 17, the reagent dispensing arm 18, and the cuvette transfer part 23, respectively. The rotary encoder part 212 includes a rotary encoder which outputs pulse signals corresponding to amounts of rotational displacements of the respective stepping motors included in the stepping motor part 211.

The fluid level detection sensor 213 is connected to the pipette 18a installed at the leading end of the reagent dispensing arm 18 and is configured to detect the contact of the lower end of the pipette 18a with the fluid level of the reagent. The sensor part 214 includes a sensor to detect that the position in the vertical direction of the pipette 18a is located at the position of the origin, and another sensor to detect that the power button 2d is pressed. The mechanism part 215 includes mechanisms for driving the cuvette supply part 15, the time-critical sample setting part 19, the heater 24, and the fluid part 26, and an air pressure source to supply pressure to the piercer 17a and the pipette 18a so as to enable the piercer 17a and the pipette 18a to perform the dispensing operations. With reference to FIG. 2, the optical information acquisition part 216 includes at least the lamp unit 27, the optical fiber 21, and the detection part 22.

A description is given of a configuration of the control device 40. As illustrated in FIG. 1, the control device 40 is formed from the display part 41, an input part 42, and a computer body 43. The control device 40 receives the optical information from the measurement part 20. Then, a processor of the control device 40 calculates the first to sixth coagulation times based on the optical information. The processor of the control device 40 calculates the first index as the value based on the first, second, and third coagulation times, and calculates the second index as the value based on the fourth, fifth, and sixth coagulation times. Meanwhile, the processor of the control device 40 executes a computer program for analyzing the blood sample. The control device 40 also functions as a device for determining the blood sample. The display part 41 displays the result of analysis obtained by the computer body 43.

Figure 6:
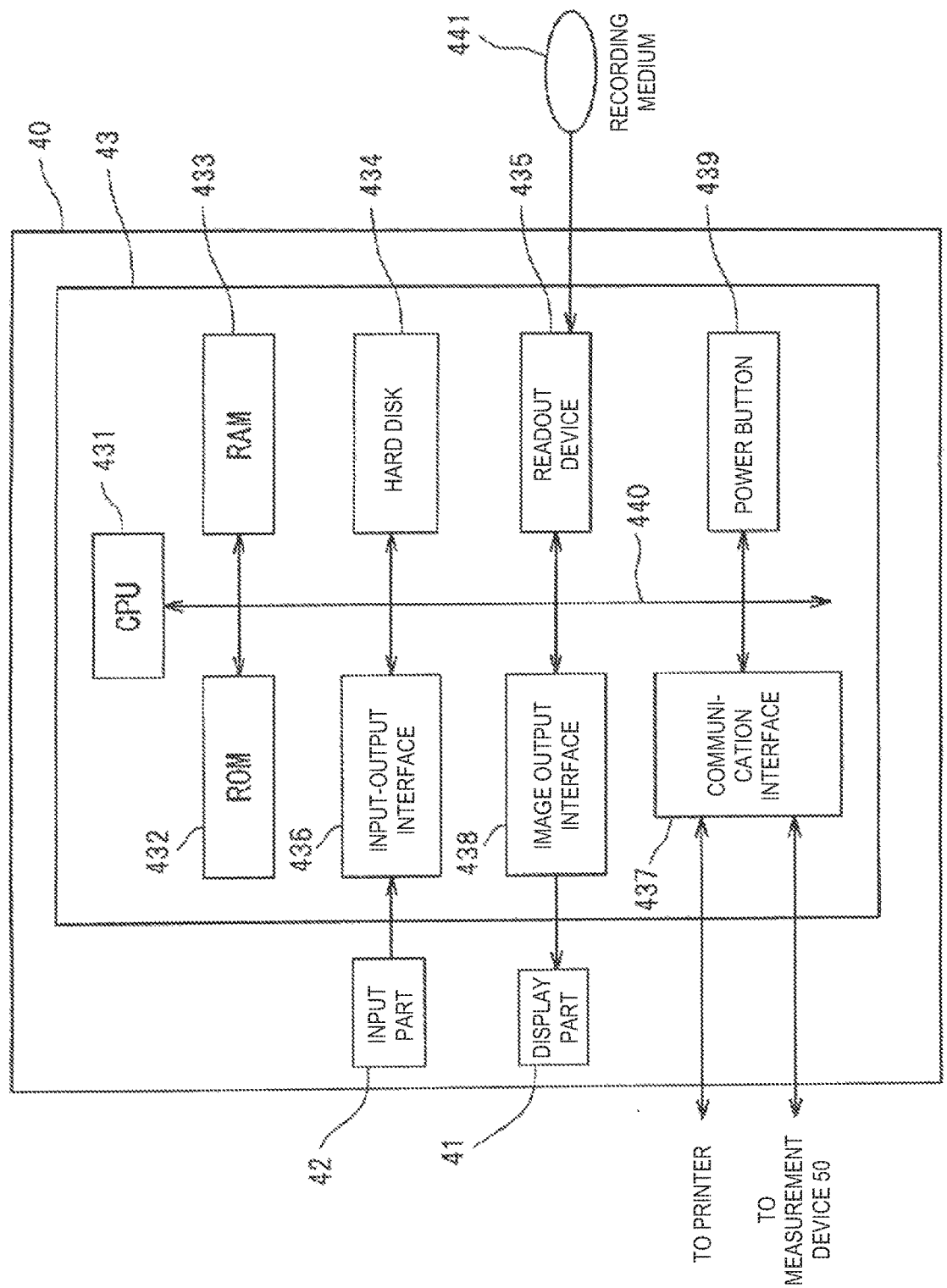
FIG. 6 is a diagram illustrating a hardware configuration of a control device of a blood sample analyzer.

As illustrated in FIG. 6, the computer body 43 of the control device 40 includes a CPU 431, a ROM 432, a RAM 433, the hard disk 434, a readout device 435, an input-output interface 436, a communication interface 437, an image output interface 438, and the power button 439. The CPU 431, the ROM 432, the RAM 433, the hard disk 434, the readout device 435, the input-output interface 436, the communication interface 437, the image output interface 438, and the power button 439 are communicably connected to one another by using a bus 440.

The CPU 431 executes computer programs stored in the ROM 432 and computer programs loaded into the RAM 433. As a consequence of execution of the computer programs for analyzing the blood sample by the CPU 431, the control device 40 functions as the device for analyzing the blood sample.

The ROM 432 is formed from a mask ROM, a PROM, an EPROM, an EEPROM, and the like. The computer programs to be executed by the CPU 431 and data used therein are recorded in the ROM 432.

The RAM 433 is formed from an SRAM, a DRAM, and the like. The RAM 433 is used for reading the computer programs recorded in the ROM 432 and the hard disk 434. In the meantime, the RAM 433 is also used as a work area of the CPU 431 when these computer programs are executed.

An operating system, the computer programs such as application programs (the compute programs for analyzing the blood sample) to be executed by the CPU 431, data used for execution of the computer programs, and details of settings of the control device 40 are installed in the hard disk 434.

The readout device 435 is formed from a flexible disk drive, a CD-ROM drive, a DVD-ROM drive, and the like. The readout device 435 can read computer programs or data recorded on a portable recording medium 441 such as a CD and a DVD.

The input-output interface 436 is formed from: a serial interface such as USB, IEEE1394, and RS-232C; a parallel interface such as SCSI and IDE Interface; and an analog interface such as a D/A converter and an A/D converter. The input part 42 such as a keyboard and a mouse is connected to the input-output interface 436. The user inputs instructions through the input part 42 and the input-output interface 436 accepts inputted signals through the input part 42.

The communication interface 437 is an Ethernet (registered trademark) interface, for example. The control device 40 can transmit printing data to a printer through the communication interface 437. The communication interface 437 is connected to the measurement part 20, and the CPU 431 performs transmission and reception of the instruction signals and the data to and from the measurement part 20 through the communication interface 437.

The image output interface 438 is connected to the display part 41 formed from an LCD, a CRT, and the like. The image output interface 438 outputs a video signal corresponding to image data to the display part 41, and the display part 41 displays an image based on the video signal outputted from the image output interface 438.

In the blood sample analyzer of one or more embodiments, the control device 40 functions as an analysis part, which acquires the first to sixth blood coagulation times based on the optical information (such as transmitted light intensity) detected by the detection part 22, and acquires the first and second index values based on the acquired coagulation times.

(Processing Procedures by Blood Sample Analyzer)

With reference to FIG. 3, in the measurement operation, the CPU 201 of the measurement part 20 temporarily stores digitalized data (the optical information) outputted from the detection part 22 (see FIG. 2) in the memory 202. A storage area in the memory 202 is subjected to area division for the respective support parts 22a. The data (the optical information) acquired at the time of irradiation of the cuvettes 104 supported by the corresponding support parts 22a with the light having a predetermined wavelength are sequentially stored in the respective areas. In this way, the data are sequentially stored in the memory 202 over a predetermined measurement period. As the measurement period goes by, the CPU 201 aborts the data storage in the memory 202 and transmits the stored data to the control device 40 through the communication interface 203. The control device 40 conducts the analysis by processing the received data, and displays a result of analysis on the display part 41.

Figure 7A:
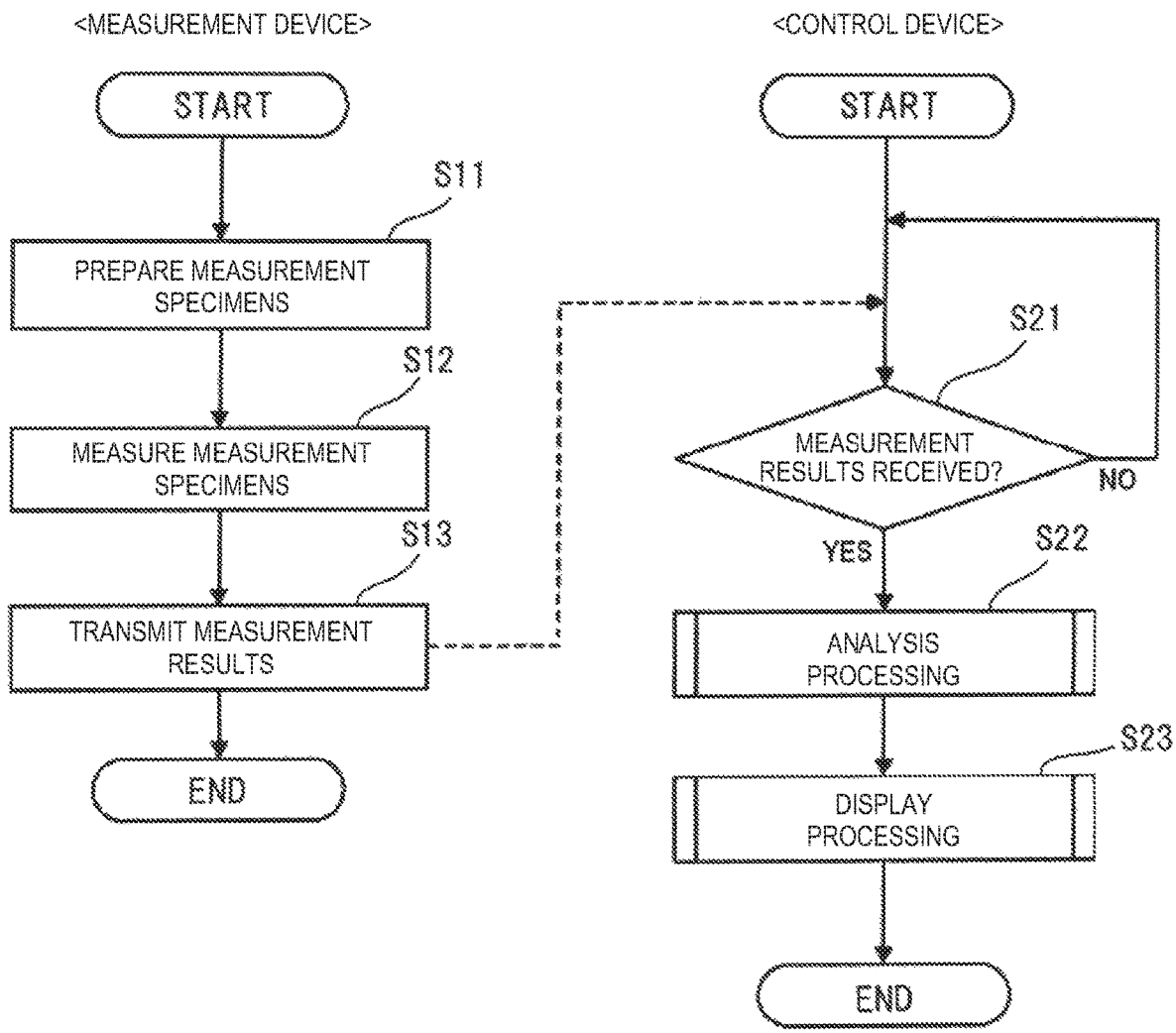
FIG. 7A is a flowchart illustrating measurement processing of a blood sample by a blood sample analyzer.

The processing by the measurement part 20 is mainly conducted under control of the CPU 201 of the measurement part 20, while the processing by the control device 40 is mainly conducted under control of the CPU 431 of the control device 40. However, one or more embodiments is not limited to this configuration. The processing by the measurement part 20 may be conducted under control of the CPU 431 of the control device 40. With reference to FIG. 7A, when the measurement processing is started, the measurement part 20 aspirates the blood sample (the plasma) of the subject from the sample container 101 transported by the sample transporter 30 as described above, and dispenses this sample into an empty cuvette 104 on the cuvette table 13. Meanwhile, the measurement part 20 aspirates the normal blood sample (the plasma) from the reagent container 103, which contains the normal blood sample and is stored in the reagent storage part, and dispenses this sample into another empty cuvette 104 on the cuvette table 13. Here, the mixed sample of the blood sample of the subject and the normal blood sample may be prepared in accordance with a hand method conducted by the user in advance and put into the sample container 101. Alternatively, the mixed sample may be prepared by the measurement part 20. The preparation of the mixed sample by the measurement part 20 is conducted as follows, for example. The measurement part 20 aspirates a predetermined amount of the normal blood sample (the plasma) from the reagent container 103 containing the normal blood sample, and dispenses this sample into the vacant cuvette 104. Then, the measurement part 20 aspirates a predetermined amount of the blood sample (the plasma) of the subject from the sample container 101 containing the blood sample, and dispenses this sample into the vacant cuvette 104 containing the normal blood sample and agitates the mixture, thereby preparing the mixed sample. One or more embodiments employs the two types of the first and second coagulation time measurement reagents. Accordingly, two cuvettes 104 containing the blood sample of the subject, two cuvettes 104 containing the normal blood sample, and two cuvettes 104 containing the mixed sample are to be prepared.

Subsequently, the measurement part 20 transfers the cuvettes 104 that contain the blood sample of the subject, the normal blood sample, and the mixed sample, respectively, to the heater 24 to heat the samples in the cuvettes 104 at the predetermined temperature (such as 37° C.). Then, the measurement part 20 prepares the first to third measurement specimens by adding the first coagulation time measurement reagent (the first partial reagent and the second partial reagent) to the cuvettes 104 containing the respective blood samples. Moreover, the measurement part 20 prepares the fourth to sixth measurement specimens by adding the second coagulation time measurement reagent (the third partial reagent and the fourth partial reagent) to the rest of the cuvettes 104 containing the respective blood samples (step S11).

The measurement part 20 starts the measurement of the coagulation time at the point of time when the partial reagents containing the calcium chloride aqueous solution are added to the cuvettes 104. When each of the first and the second coagulation time measurement reagents is the single liquid reagent containing calcium ions or the snake venom, the measurement of the coagulation time is started at the point of time when the reagents are added. Thereafter, the measurement part 20 transfers the cuvettes 104 with the added reagents to the detection part 22 where the measurement specimens are measured by irradiating the cuvettes 104 with the light (step S12). In this measurement, the data (the amounts of scattered light or the amounts of transmitted light) based on the light with the wavelength of 660 nm are sequentially stored in the memory 202 during the measurement period. At this time, the data to be stored in the memory 202 are linked with the elapsed time from the point of time when the reagents are added. Then, as the measurement period goes by, the measurement part 20 aborts the measurement and transmits the measurement results (the data) stored in the memory 202 to the control device 40 (step S13).

As described above, the coagulation time of the normal blood sample may be the predetermined value measured and recorded in advance by using each of the first and second coagulation time measurement reagents. Accordingly, in one or more embodiments, the measurement part 20 does not always have to measure the coagulation time of the normal blood samples. In this case, the predetermined values are stored in the hard disk 434 in advance as the second and fifth coagulation times.

When the control device 40 receives the measurement results (the data) from the measurement part 20 (step S21: yes), the control device 40 executes analysis processing on the received measurement results (step S22). Specifically, the control device 40 calculates the first to third coagulation times and the first index value regarding the measurement specimens to which the first coagulation time measurement reagent is added, and calculates the fourth to sixth coagulation times and the second index value regarding the measurement specimens to which the second coagulation time measurement reagent is added. After executing the analysis processing (step S22), the control device 40 executes display processing of the results of analysis (step S23).

Figure 7B:
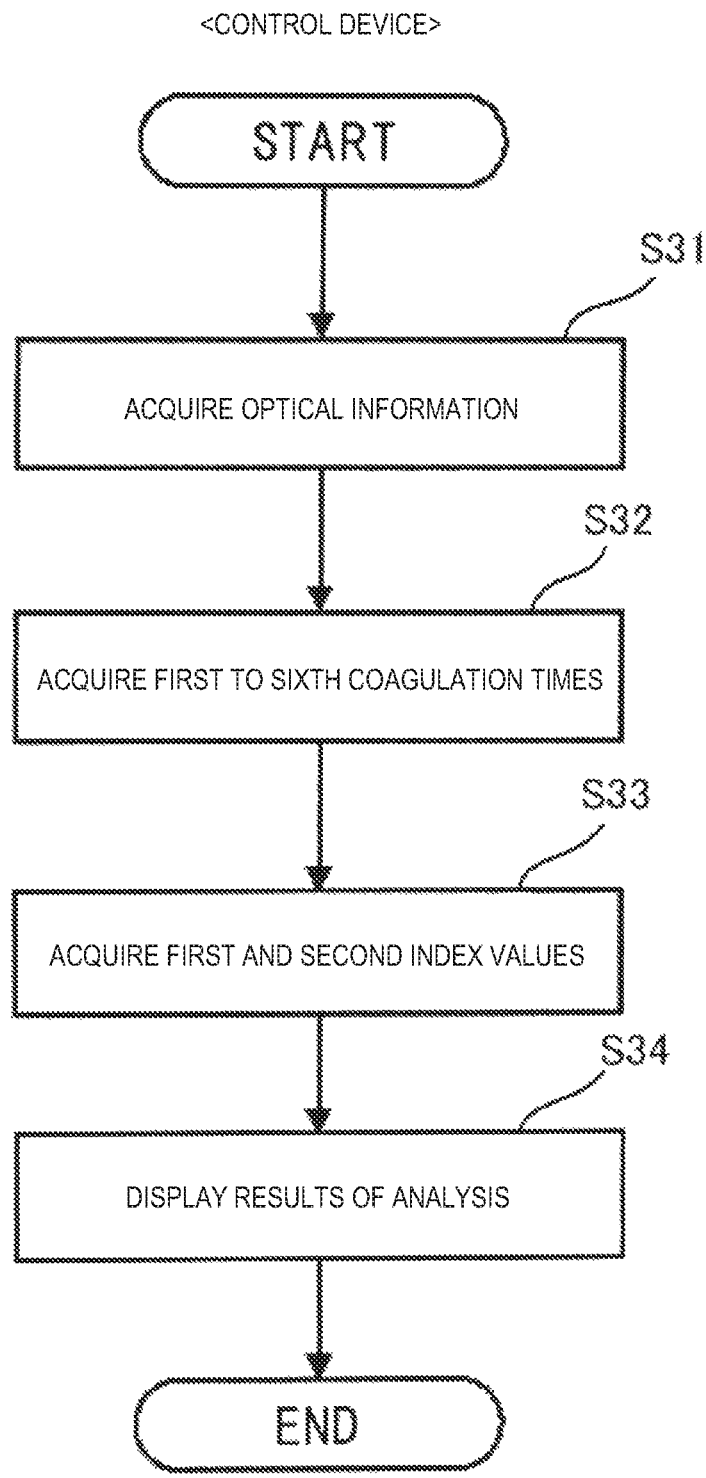
FIG. 7B is a flowchart illustrating procedures of measurement data analysis processing and analysis result display processing.

A description is given of the aforementioned analysis processing and display processing with reference to FIG. 7B. In step S31, the CPU 431 of the control device 40 acquires the optical information (the scattered light intensity or any of the transmittance and the absorbance) based on the data (the amounts of scattered light or the amounts of transmitted light) received from the measurement part 20. In step S32, the CPU 431 calculates the first to sixth coagulation times from the acquired optical information in accordance with the formulae stored in the hard disk 434 for calculating the coagulation time, and stores values thus calculated into the hard disk 434. In step S33, the CPU 431 calculates the first index value from the values of the first to third coagulation times in accordance with the formula stored in the hard disk 434 for calculating the first index value. Likewise, the CPU 431 calculates the second index value from the values of the fourth to sixth coagulation times in accordance with the formula stored in the hard disk 434 for calculating the second index value. Then, the CPU 431 stores the first and second index values thus calculated into the hard disk 434. In step S34, the CPU 431 causes the display part 41 to display at least the first and second index values as the results of analysis. The CPU 431 may further cause the display part 41 to display the first to sixth coagulation times. Meanwhile, the CPU 431 may cause the display part 41 to display a graph plotting the first to third coagulation times. This graph is preferably a graph in which the horizontal axis indicates the ratio (v/v %) of the blood sample of the subject in the respective blood samples and the vertical axis indicates the coagulation time (seconds).

A screen displaying the results of measurement of the coagulation time of the respective samples is described with reference to FIG. 8 as an example of a screen to display the results of analysis. The screen illustrated in FIG. 8 displays items of, rack number and position, sample number, starting time and ending time of measurement, coagulation time (LA1 1-1 sec) with first coagulation time measurement reagent, and coagulation time (LA2 1-1 sec) with second coagulation time measurement reagent. However, one or more embodiments are not limited only to these items. In FIG. 8, a sample having the sample number provided with "1-1" represents the mixed sample in which the ratio of the blood sample of the subject is 50% (v/v). In one or more embodiments, the first and second index values may be displayed on this screen. The user can employ the first and second index values displayed on the screen for determining whether or not the blood sample of the subject is the DAC sample.

Figure 9:
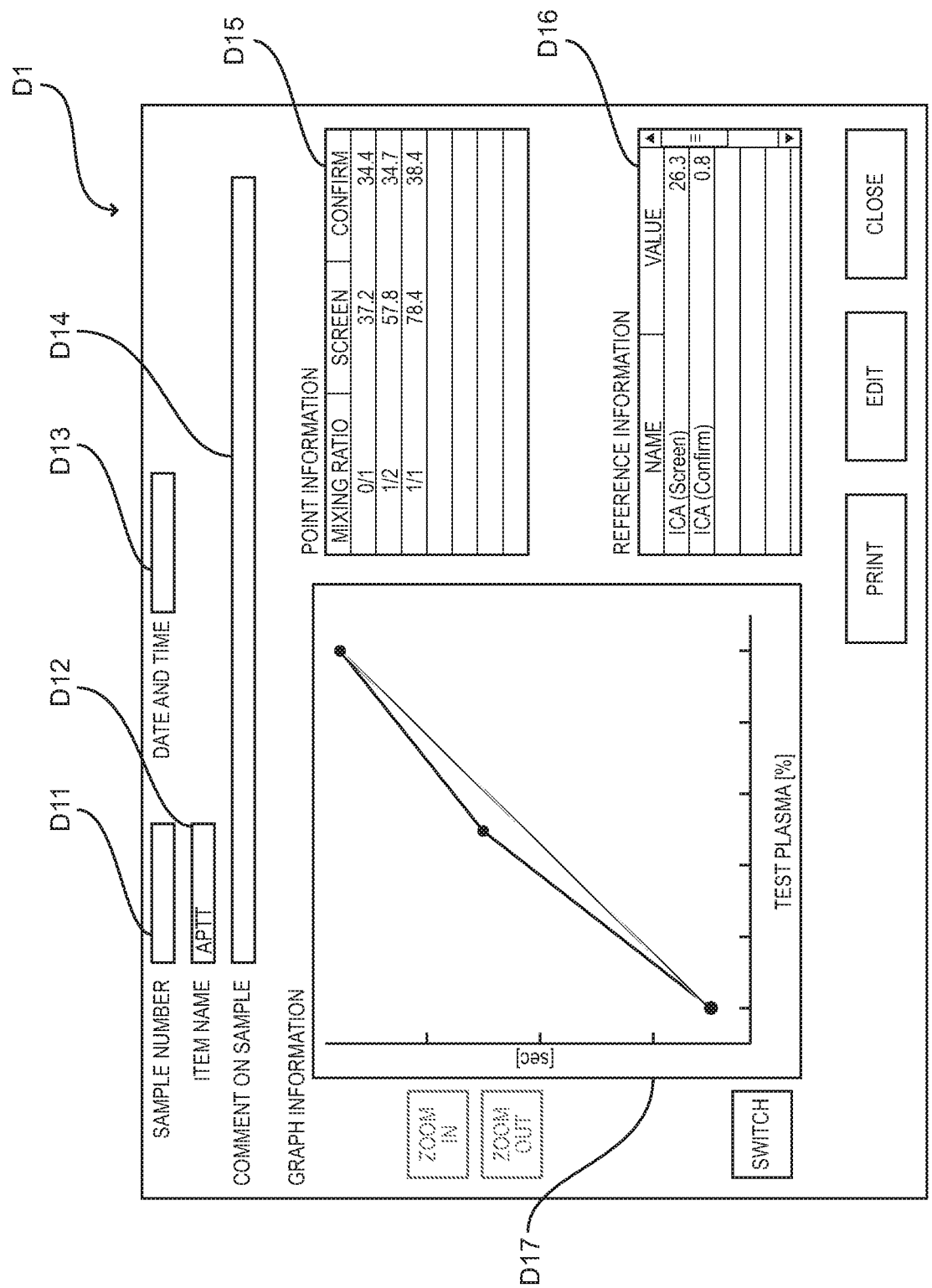
FIG. 9 is a diagram illustrating an example of a screen that displays measurement results by a blood sample analyzer.

Alternatively, the first and second index values may be displayed on a different screen. For example, when the user selects a certain blood sample on the screen illustrated in FIG. 8 by using the input part 42, the first and second index values may be displayed on a screen such as one illustrated in FIG. 9. With reference to FIG. 9, a screen D1 includes: a region D11 to display a sample number; a region D12 to display a measurement item name; a region D13 to display date and time of measurement; a region D14 to display a comment on the sample; a region D15 to display the coagulation times and mixing ratios; a region D16 to display reference information; and a region D17 to display the graph plotting the coagulation times. In FIG. 9, the mixing ratios and the coagulation times with the LA screening reagent (the first coagulation time measurement reagent) and the confirmation test reagent (the second coagulation time measurement reagent) are displayed in the region D15. In a column for the mixing ratios, a remark "0/1" represents the normal blood sample, a remark "1/2" represents the mixed sample with the ratio of the plasma of the subject equal to 50% (v/v), and a remark "1/1" presents the blood sample of the subject. In FIG. 9, the ICA values are displayed in the region D16 as the first and second index values. In one or more embodiments, the graph plotting the coagulation times with the first coagulation time measurement reagent is preferably displayed in the region D17 because a cross-mixing test is usually conducted by employing a screening reagent with a low phospholipid concentration in this technical field.

Figure 10A:
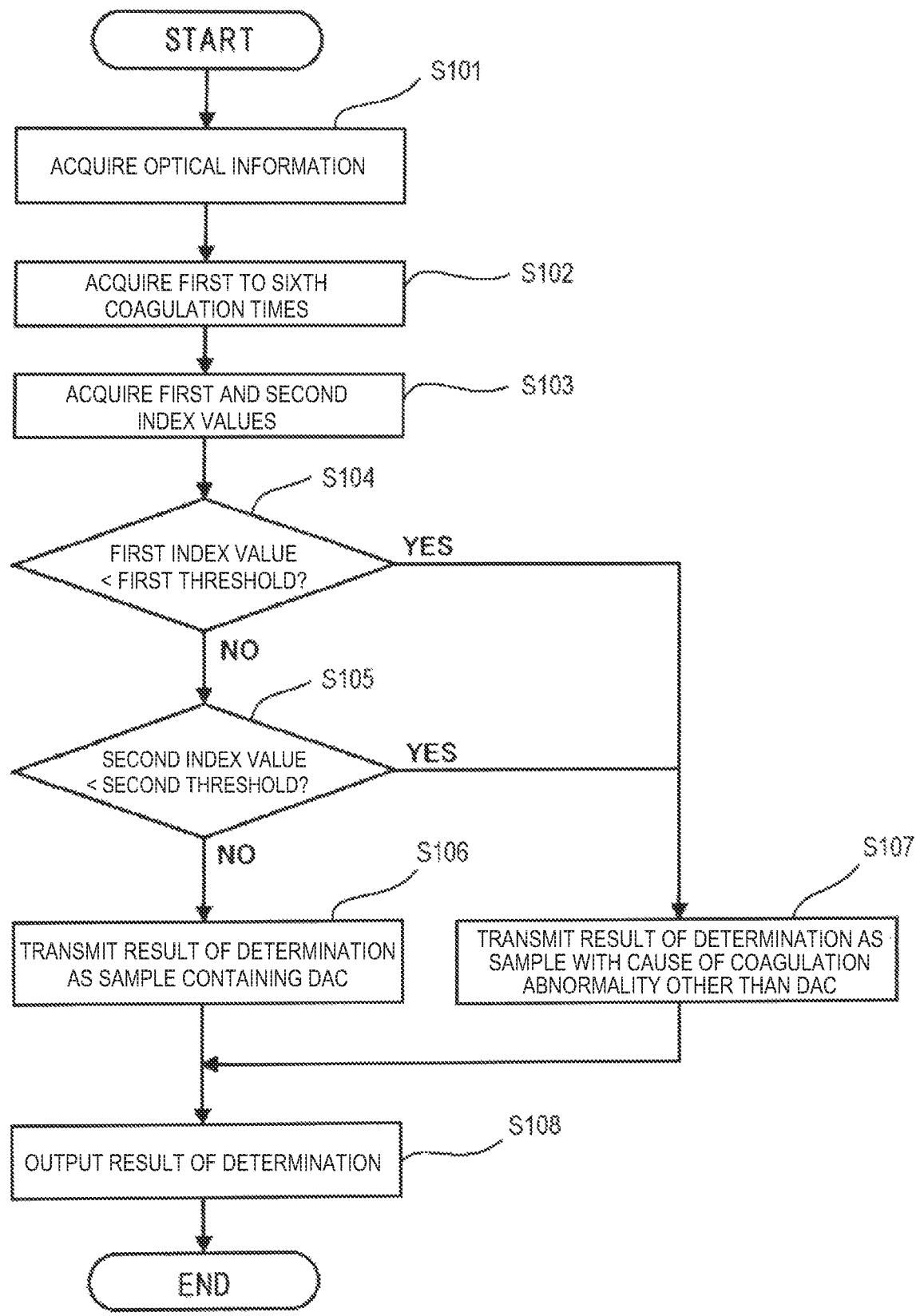
FIG. 10A is a flowchart illustrating blood sample analysis processing by a blood sample analyzer.

The device of one or more embodiments may be configured to determine whether or not the blood sample of the subject is the blood sample containing the DAC based on the acquired first and second index values, and to output a result of determination as reference information. A flow of the determination by the control device is described below with reference to FIG. 10A. FIG. 10A illustrates a flow of processing in the case of determining the blood sample from the results of measurement of the blood sample of the subject, the normal blood sample, and the mixed sample obtained by mixing those samples at the volume ratio of 1:1. Here, the case of acquiring the values calculated by the aforementioned formulae (1) and (2) as the first and second index values, respectively, and determining the blood sample by comparing the acquired values with the first and second thresholds is explained as an example. However, one or more embodiments is not limited only to this example. The mixing ratio of the mixed sample and the types of the index values can be changed as appropriate with reference to the above statements regarding the method of one or more embodiments.

In step S101, the CPU 431 of the control device 40 acquires the optical information (the scattered light intensity or any of the transmittance and the absorbance) based on the data (the amounts of scattered light or the amounts of transmitted light) received from the measurement part 20. In step S102, a calculator 403 calculates the first to sixth coagulation times from the optical information acquired by the CPU 431 in accordance with the formulae stored in the hard disk 434 for calculating the coagulation time. In step S103, the CPU 431 calculates the first index value from the first to third coagulation times in accordance with the formula (1) stored in the hard disk 434. Meanwhile, the CPU 431 calculates the second index value from the fourth to sixth coagulation times in accordance with the formula (2) stored in the hard disk 434.

In step S104, the CPU 431 compares the calculated first index value with the first threshold stored in the hard disk 434. When the first index value is not lower than the first threshold (in other words, when the first index value is higher than the first threshold or equal to the first threshold), the processing proceeds to step S105. In step S105, the CPU 431 compares the calculated second index value with the second threshold stored in the hard disk 434. When the second index value is not lower than the second threshold (in other words, when the second index value is higher than the second threshold or equal to the second threshold), the processing proceeds to step S106. In step S106, the CPU 431 sends the image output interface 438 a result of determination that the blood sample of the subject is the sample containing the DAC.

In step S104, if the first index value is lower than the first threshold, then the processing proceeds to step S107. Meanwhile, in step SS105, if the second index value is lower than the second threshold, then the processing proceeds to step S107. In step S107, the CPU 431 sends the image output interface 438 a result of determination that the blood sample of the subject is the sample with a cause of coagulation abnormality other than the DAC.

In step S108, the image output interface 438 outputs the result of determination and causes the display part 41 to display the result or causes a printer to print the result. Alternatively, the result of determination may be outputted in audio. The reference information concerning the result of determination may be textual information such as "suspected to contain DAC". The reference information may also be a sign such as a flag. In this way, it is possible to provide the user with the result of determination as the reference information concerning the blood sample of the subject. Furthermore, the first and second thresholds may be displayed as the reference information. Here, determination of the blood sample is preferably conducted in consideration of not only the result of determination by the analyzer of one or more embodiments but also information on other test results and the like. In this regard, the result of determination by the analyzer of one or more embodiments and the predetermined thresholds may be displayed with an additional mark "(reference)" so as to indicate the relevant information is the reference information.

In one or more embodiments, when the control device 40 determines that the blood sample of the subject is the blood sample containing the cause of coagulation abnormality other than the DAC, the control device 40 can also determine whether or not the blood sample of the subject is the blood sample containing the LA or the blood sample deficient in the coagulation factor based on the first and second index values. A flow of the determination by the control device is described below with reference to FIG. 10B.

Figure 10B:
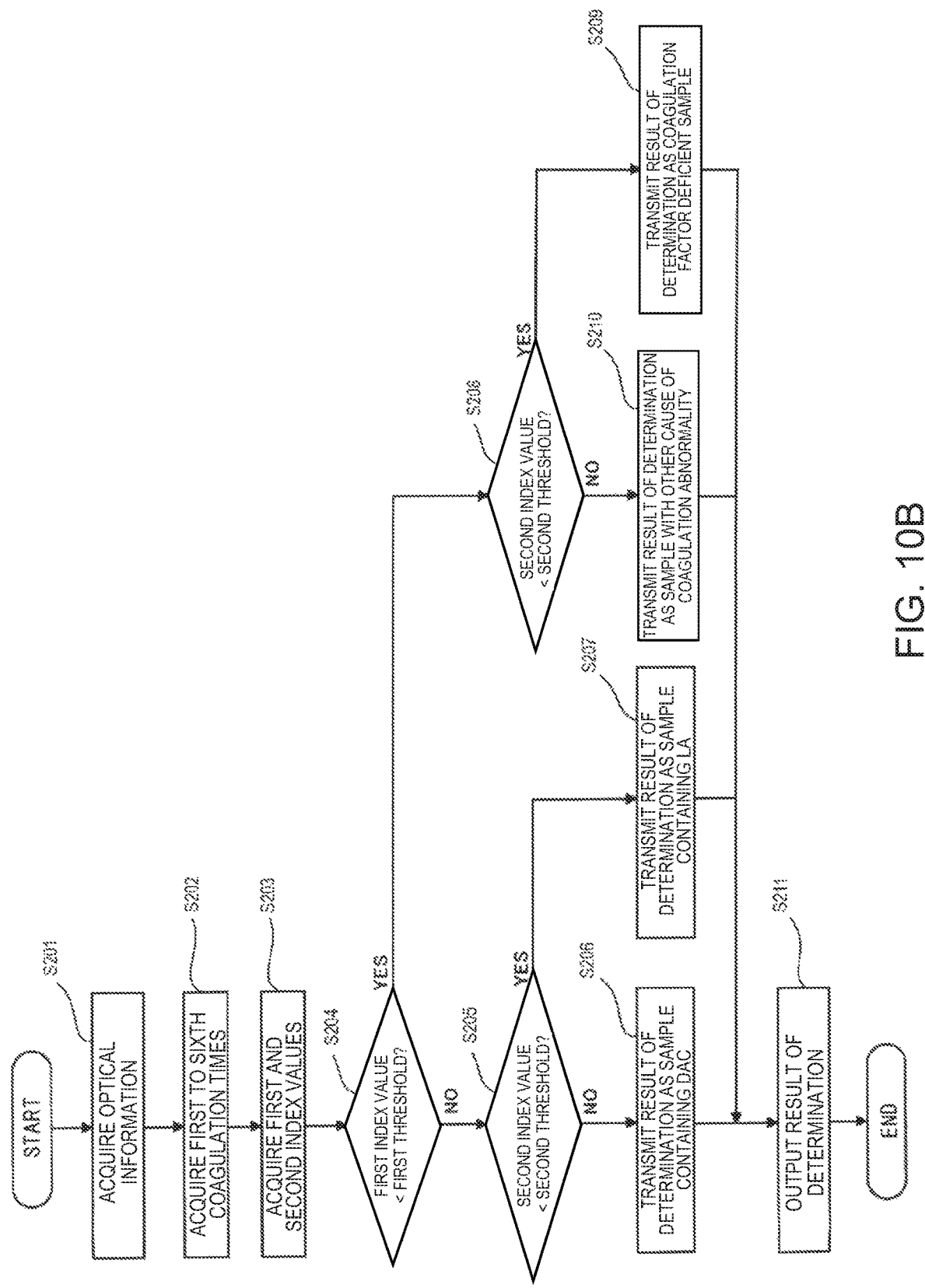
FIG. 10B is a flowchart illustrating blood sample analysis processing by a blood sample analyzer.

Details of step S201, step S202, and step S203 illustrated in FIG. 10B are the same as those discussed in connection with step S101, step S102, and step S103 in FIG. 10A. In step S204, the CPU 431 compares the calculated first index value with the first threshold stored in the hard disk 434. When the first index value is not lower than the first threshold (in other words, when the first index value is higher than the first threshold or equal to the first threshold), the processing proceeds to step S205. In step S205, the CPU 431 compares the calculated second index value with the second threshold stored in the hard disk 434. When the second index value is not lower than the second threshold (in other words, when the second index value is higher than the second threshold or equal to the second threshold), the processing proceeds to step S206. In step S206, the CPU 431 sends the image output interface 438 a result of determination that the blood sample of the subject is the sample containing the DAC.

In step S205, if the second index value is lower than the second threshold, then the processing proceeds to step S207. In step S207, the CPU 431 sends the image output interface 438 a result of determination that the blood sample of the subject is the sample containing the LA.

In step S204, if the first index value is lower than the first threshold, then the processing proceeds to step S208. In step S208, the CPU 431 compares the calculated second index value with the second threshold stored in the hard disk 434. If the second index value is lower than the second threshold, then the processing proceeds to step S209. In step S209, the CPU 431 sends the image output interface 438 a result of determination that the blood sample of the subject is the sample deficient in the coagulation factor.

In step S208, when the second index value is not lower than the second threshold (in other words, when the second index value is higher than the second threshold or equal to the second threshold), the processing proceeds to step S210. In step S210, the CPU 431 sends the image output interface 438 a result of determination that the blood sample of the subject is a sample with a cause of coagulation abnormality other than those mentioned above.

Details of step S211 are the same as those details discussed in connection with step S108. The result of determination may be displayed in texts such as "suspected to contain DAC", "suspected to contain LA", "suspected to be deficient in coagulation factor", and so forth on the screen of the display part 41.

Now, one or more embodiments are described below in further detail with reference to examples. It is to be noted, however, that the invention is not limited to these examples.

EXAMPLES

Example 1

A mixing test is conducted by using two types of coagulation time measurement reagents having different phospholipid concentrations to obtain two types of index values. It is then investigated whether or not the aforementioned procedures can discriminate between a blood sample containing the DAC and a blood sample containing a different cause of coagulation abnormality such as the LA.

(1) Reagents and Samples (1.1) Coagulation Time Measurement Reagents

As the coagulation time measurement reagents, LA1 Screening Reagent (Lot No. 549855AA, Siemens: hereinafter referred to as a "first reagent") and LA2 Confirm Reagent (Lot No. 548732A, Siemens: hereinafter referred to as a "second reagent") are used. The first reagent is an LA screening reagent based on the dRVVT measurement. The first reagent contains the Russell's viper venom and the phospholipid. The second reagent is an LA confirmation test reagent based on the dRVVT measurement. The second reagent contains the Russell's viper venom and the phospholipid at a higher concentration than that in the first reagent.

(1.2) Blood Samples

As the blood samples of the subject, LA-containing plasma samples listed in Table 1 (13 samples), rivaroxaban-containing plasma samples listed in Table 2 (10 samples: hereinafter also referred to as "DAC-containing plasma samples"), and plasma samples deficient in coagulation factors (any of Factor II, Factor V, Factor VII, and Factor X) listed in Table 3 are used. In this example, in order to obtain samples with various degrees of coagulation factor deficiencies, the respective coagulation factor deficient plasma samples and the normal plasma are mixed at various ratios to prepare the plasma samples with the ratios of the respective coagulation factors at 20%, 10%, 5%, 2.5%, and below 1% (20 samples: hereinafter also referred to as "coagulation factor deficient plasma samples"). Note that the plasma samples each with the ratio of the corresponding coagulation factor below 1% are identical to the respective plasma samples listed in Table 3. These plasma samples are hereinafter collectively referred to as "test plasma samples" as well. Incidentally, Control N (Lot No. 503197A: Sysmex Corporation), which is normal plasma, is used as the normal blood sample.

TABLE 1

| Product name | Supplier | Lot number |
| --- | --- | --- |
| LA Control 1 Low | Siemens | 546061B |
| | | 546060B |
| | | 546064A |
| | | 546065A |
| | | 546066A |
| LA Control 2 High | Siemens | 54932BA |
| | | 545936A |
| | | 545937B |
| LA weak positive | PBI | WL-022 |
| | | WL-023 |
| | | WL-024 |
| LA positive | PBI | 6247 |
| | | 6248 |

TABLE 2

| Product name | Supplier | Lot number |
| --- | --- | --- |
| Rivaroxaban Control Plasma 1 | HBM | 43202-1 |
| | | 43604-1 |
| Rivaroxaban Control Plasma 2 | HBM | 43202-2 |
| | | 43604-2 |
| Rivaroxaban Calibrator Plasma 2 | HBM | 42201-2 |
| Rivaroxaban Calibrator Plasma 3 | HBM | 42201-3 |
| Rivaroxaban Low Control Plasma 1 | HBM | 42203-1 |
| Rivaroxaban Low Control Plasma 2 | HBM | 42203-2 |
| Rivaroxaban Low Calibrator Plasma 2 | HBM | 44502-2 |
| Rivaroxaban Low Calibrator Plasma 3 | HBM | 44502-3 |

TABLE 3

| Product name | Supplier | Lot number |
| --- | --- | --- |
| CRYOcheck™ Factor II deficient plasma | PBI | D2-35 |
| CRYOcheck™ Factor V deficient plasma | PBI | D5-35 |
| CRYOcheck™ Factor VII deficient plasma | PBI | D7-27 |
| CRYOcheck™ Factor X deficient plasma | PBI | D10-27 |

(2) Measurement of Coagulation Time

Each test plasma sample (100 μL) is heated at 37° C. for four minutes. Then, the sample is mixed with the first reagent (100 μL) and subjected to measurement of the first coagulation time. Each normal plasma sample (100 μL) is heated at 37° C. for four minutes. Then, the sample is mixed with the first reagent (100 μL) and subjected to measurement of the second coagulation time. The normal plasma sample (50 μL) is mixed with the test plasma sample (50 μL) and the mixed plasma sample thus obtained is heated at 37° C. for four minutes. Then, the sample is mixed with the first reagent (100 μL) and subjected to measurement of the third coagulation time. Meanwhile, the fourth coagulation time is measured with the test plasma sample, the fifth coagulation time is measured with the normal plasma sample, and the sixth coagulation time is measured with the mixed plasma sample in a similar way to those described above except that the second reagent is used instead of the first reagent. The measurement of each coagulation time is conducted by using a fully automatic coagulation time measurement device CS-5100 (Sysmex Corporation).

(3) Acquisition of Index Values

The first and second index values are acquired from the coagulation times measured by using each sample and in accordance with the following formulae (3) and (4). Note that the first index value is the ICA (Index of Circulating Anticoagulant) known as the quantification index in the mixing test for the LA detection:

(the first index value)=$[(C-B)/A] \times 100$ . . . formula (3); and (the second index value)=$[(F-E)/A] \times 100$ . . . formula (4) (in which, A: the first coagulation time, B: the second coagulation time, C: the third coagulation time of the mixed plasma sample in which the ratio of the test plasma sample is 50% (v/v); D: the fourth coagulation time, E: the fifth coagulation time, and F: the sixth coagulation time of the mixed plasma sample in which the ratio of the test plasma sample is 50% (v/v)).

(4) Results

The second coagulation time turns out to be 37.2 seconds while the fifth coagulation time turns out to be 34.4 seconds. As an example of the results of measurement of the test plasma samples, the coagulation times (the first, third, fourth, and sixth coagulation times) and the first and second index values of a few of the samples are listed in Table 4. The first and second index values in an LA group, a DAC group, and a coagulation factor deficient group are plotted in FIGS. 11A and 11B, respectively.

TABLE 4

| Blood sample (Lot number) | LA-containing plasma (545936A) | DAC-containing plasma (43202-2) | FII-deficient (below 1%) plasma (D2-35) |
| --- | --- | --- | --- |
| First coagulation time (sec) | 78.4 | 166.2 | 138.2 |
| Third coagulation time (sec) | 57.8 | 88.6 | 42.9 |
| Fourth coagulation time (sec) | 38.4 | 84.0 | 115.3 |
| Sixth coagulation time (sec) | 34.7 | 57.2 | 40.2 |
| First index value (%) | 26.3 | 30.9 | 4.1 |
| Second index value (%) | 0.8 | 27.1 | 5.0 |

Figure 11A:
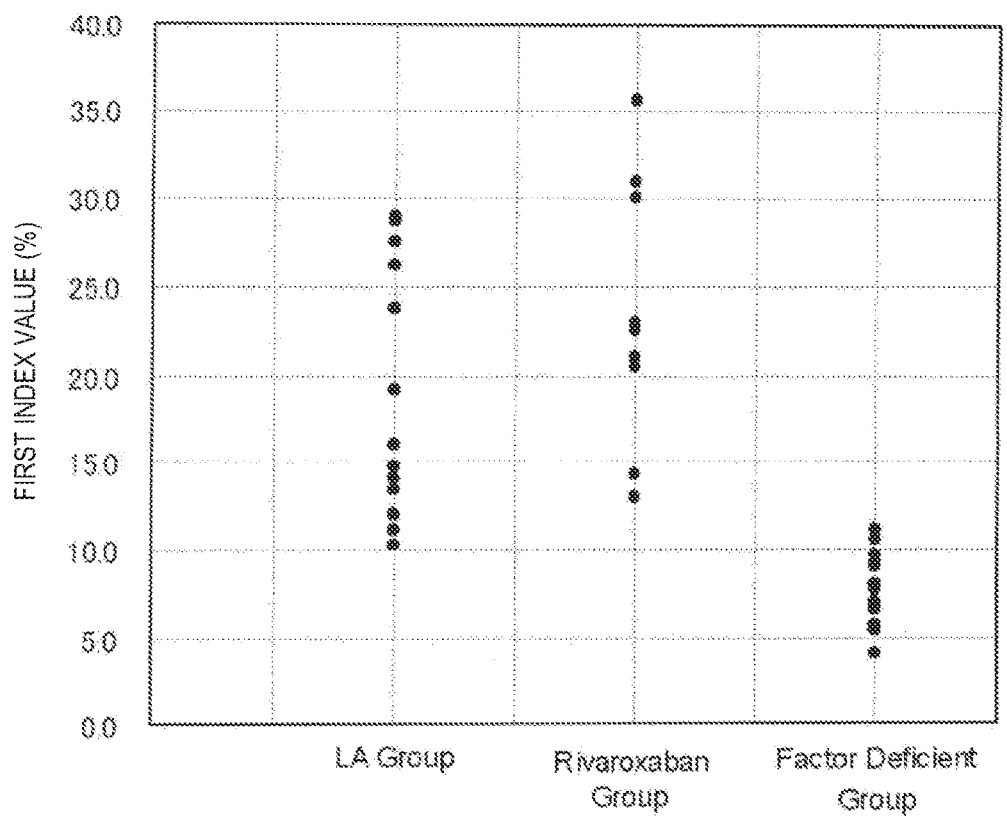
FIG. 11A is a diagram illustrating distribution of first index values (ICA) in a DAC sample, an LA sample, and a coagulation factor deficient sample in the case of using a coagulation time measurement reagent with a low phospholipid concentration.
Figure 11B:
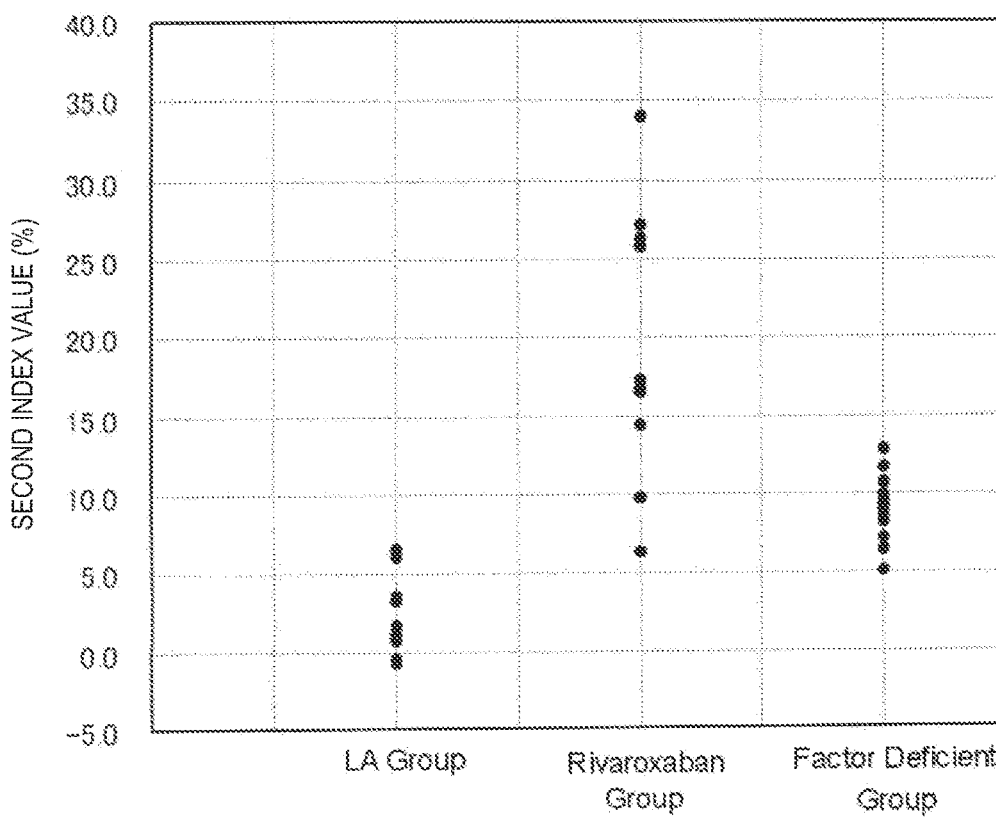
FIG. 11B is a diagram illustrating distribution of second index values (ICA) in a DAC sample, an LA sample, and a coagulation factor deficient sample in the case of using a coagulation time measurement reagent with a high phospholipid concentration.

As plotted in FIG. 11A, it turns out that the first index values tend to be high in the LA group as well as the DAC group and low in the coagulation factor deficient group. As plotted in FIG. 11B, it turns out that the second index values tend to be high in the DAC group and low in the LA group as well as the coagulation factor deficient group. These results reveal that each of the DAC group, the LA group, and the coagulation factor deficient group are characterized by the magnitudes of the first and second index values, respectively. For example, it turns out that the DAC group tends to have both the high first index value and the high second index value. This tendency suggests that it is possible to determine whether or not the blood sample of the subject is the blood sample containing the DAC by subjecting the blood sample to the mixing test by using the two types of coagulation time measurement reagents having the different phospholipid concentrations and thus obtaining the two types of the index values.

An investigation is made as to whether or not it is possible to differentiate between the causes of coagulation abnormality by use of the first and second index values. To be more precise, the aforementioned test plasma samples are classified based on a matrix listed in Table 5 and sensitivity and specificity are calculated in terms of the classification result. Cutoff values (thresholds) of the first and second index values are set to 12.0, respectively. Results are listed in Table 6.

TABLE 5

|  | Second index value equal to or above 12.0 | Second index value below 12.0 |
|---|---|---|
| First index value equal to or above 12.0 | DAC-containing sample | LA-containing sample |
| First index value below 12.0 | other | Coagulation factor deficient sample |

TABLE 6

|  | DAC-containing plasma | LA-containing plasma | Coagulation factor deficient plasma |
|---|---|---|---|
| Sensitivity (%) | 80.0 | 84.6 | 93.3 |
| Specificity (%) | 100.0 | 92.0 | 91.3 |

As described above, it is made clear that it is possible to determine at high accuracy whether the blood sample suspected to have coagulation abnormality is the blood sample containing the DAC, the blood sample containing the LA, or the blood sample deficient in the coagulation factor based on the result of comparison between each of the first and second index value with the corresponding threshold.

The invention claimed is:

1. A determination method for determining whether a blood sample of a subject contains a direct anticoagulant, the method comprising:
   acquiring:
      a first coagulation time comprising a coagulation time of the blood sample of the subject;
      a second coagulation time comprising a coagulation time of a normal blood sample having normal blood coagulation; and
      a third coagulation time comprising a coagulation time of a mixed sample comprising the blood sample of the subject and the normal blood sample;
   acquiring:
      a fourth coagulation time comprising a coagulation time of the blood sample of the subject;
      a fifth coagulation time comprising a coagulation time of the normal blood sample; and
      a sixth coagulation time comprising a coagulation time of the mixed sample;
   acquiring:
      a first index value from the first coagulation time, the second coagulation time, and the third coagulation time; and
      a second index value from the fourth coagulation time, the fifth coagulation time, and the sixth coagulation time; and
   determining whether the blood sample of the subject is a blood sample containing the direct anticoagulant by comparing the first index value with a first threshold and by comparing the second index value with a second threshold, wherein
   the first coagulation time, the second coagulation time, and the third coagulation time are coagulation times measured by using a first coagulation time measurement reagent,
   the fourth coagulation time, the fifth coagulation time, and the sixth coagulation time are coagulation times measured by using a second coagulation time measurement reagent,
   the first coagulation time measurement reagent contains a phospholipid and the second coagulation time measurement reagent contains a phospholipid at a concentration higher than a concentration of the phospholipid in the first coagulation time measurement reagent,
   the first index value is indicative of, when compared with the first threshold, whether or not the blood sample of the subject is a blood sample containing the direct anticoagulant or a lupus anticoagulant, and
   the second index value is indicative of, when compared with the second threshold, whether or not the blood sample of the subject is a blood sample containing the direct anticoagulant.

2. The method according to claim 1, wherein
   acquiring the first coagulation time comprises measuring a first measurement specimen obtained by mixing the blood sample of the subject with the first coagulation time measurement reagent,
   acquiring the second coagulation time comprises measuring a second measurement specimen obtained by mixing the normal blood sample with the first coagulation time measurement reagent, and
   acquiring the third coagulation time comprises measuring a third measurement specimen obtained by mixing the mixed sample with the first coagulation time measurement reagent.

3. The method according to claim 1, wherein
   acquiring the fourth coagulation time comprises measuring a fourth measurement specimen obtained by mixing the blood sample of the subject with the second coagulation time measurement reagent,
   acquiring the fifth coagulation time comprises measuring a fifth measurement specimen obtained by mixing the normal blood sample with the second coagulation time measurement reagent, and
   acquiring the sixth coagulation time comprises measuring a sixth measurement specimen obtained by mixing the mixed sample with the second coagulation time measurement reagent.

4. The method according to claim 1, wherein
   acquiring the first coagulation time comprises measuring a first measurement specimen obtained by mixing the blood sample of the subject with the first coagulation time measurement reagent,
   the second coagulation time is a predetermined coagulation time of the normal blood sample with the first coagulation time measurement reagent, and
   acquiring the third coagulation time comprises measuring a third measurement specimen obtained by mixing the mixed sample with the first coagulation time measurement reagent.

5. The method according to claim 1, wherein
   acquiring the fourth coagulation time comprises measuring a fourth measurement specimen obtained by mixing the blood sample of the subject with the second coagulation time measurement reagent,
   the fifth coagulation time is a predetermined coagulation time of the normal blood sample with the second coagulation time measurement reagent, and
   acquiring the sixth coagulation time comprises measuring a sixth measurement specimen obtained by mixing the mixed sample with the second coagulation time measurement reagent.

6. The determination method according to claim 1, wherein
the first index value is a value used to quantitatively evaluate a result of a mixing test comprising acquiring the first coagulation time, the second coagulation time, and the third coagulation time, wherein the first index value is acquired based on the first coagulation time, the second coagulation time, and the third coagulation time, and
the second index value is a value used to quantitatively evaluate a result of a mixing test comprising acquiring the forth coagulation time, the fifth coagulation time, and the sixth coagulation time, wherein the second index value is acquired based on the fourth coagulation time, the fifth coagulation time, and the sixth coagulation time.

7. The determination method according to claim 1, wherein
the first index value is acquired by calculating from:
a difference between the second coagulation time and the third coagulation time; and
the first coagulation time, and
the second index value is acquired by calculating from:
a difference between the fifth coagulation time and the sixth coagulation time; and
the fourth coagulation time.

8. The determination method according to claim 1, wherein
the first index value is acquired by calculating from a ratio of a difference between the second coagulation time and the third coagulation time to the first coagulation time, and
the second index value is acquired by calculating from a ratio of a difference between the fifth coagulation time and the sixth coagulation time to the fourth coagulation time.

9. The determination method according to claim 1, wherein the first index value is acquired by a formula (1) below and the second index value is acquired by a formula (2) below:

(the first index value)=[(the third coagulation time)−(the second coagulation time)]/(the first coagulation time)　　formula (1); and (the second index value)=[(the sixth coagulation time)−(the fifth coagulation time)]/(the fourth coagulation time)　　formula (2).

10. The method according to claim 1, wherein
in a condition in which the first index value is equal to or above the first threshold and the second index value is equal to or above the second threshold, the blood sample of the subject is determined to be the blood sample containing the direct anticoagulant, and
in a condition in which the first index value is below the first threshold or in a condition in which the second index value is below the second threshold, the blood sample of the subject is determined to be a blood sample with a cause of coagulation abnormality other than the direct anticoagulant.

11. The method according to claim 1, wherein
in a condition in which the first index value is equal to or above the first threshold and the second index value is below the second threshold, the blood sample of the subject is determined to be a blood sample containing the lupus anticoagulant, and
in a condition in which the first index value is below the first threshold and the second index value is below the second threshold, the blood sample of the subject is determined to be a blood sample deficient in a coagulation factor.

12. A blood sample analyzer comprising:
a measurement part configured to:
prepare a first measurement specimen from a blood sample of a subject and from a first coagulation time measurement reagent, a second measurement specimen from a normal blood sample having normal blood coagulation and from the first coagulation time measurement reagent, a third measurement specimen from a mixed sample obtained by mixing the blood sample of the subject with the normal blood sample and from the first coagulation time measurement reagent, a fourth measurement specimen from the blood sample of the subject and from a second coagulation time measurement reagent, a fifth measurement specimen from the normal blood sample and from the second coagulation time measurement reagent, and a sixth measurement specimen from the mixed sample and from the second coagulation time measurement reagent; and
acquire measurement data from the first, second, third, fourth fifth, and sixth measurement specimens; and
an analysis part comprising a processor, wherein the processor is programmed to:
acquire a first, second, third, fourth fifth, and sixth coagulation time from the measurement data;
acquire a first index value from the first coagulation time, the second coagulation time, and the third coagulation time;
acquire a second index value from the fourth coagulation time, the fifth coagulation time, and the sixth coagulation time; and
determine whether the blood sample of the subject is a blood sample containing a direct anticoagulant by comparing the first index value with a first threshold and by comparing the second index value with a second threshold, wherein
the first coagulation time measurement reagent contains a phospholipid and the second coagulation time measurement reagent contains a phospholipid at a concentration higher than a concentration of the phospholipid in the first coagulation time measurement reagent,
the first index value is indicative of, when compared with the first threshold, whether or not the blood sample of the subject is a blood sample containing either the direct anticoagulant, or a lupus anticoagulant, and
the second index value is indicative of, when compared with the second threshold, whether or not the blood sample of the subject is a blood sample containing the direct anticoagulant.

13. The blood sample analyzer according to claim 12, further comprising:
a display part.

14. The blood sample analyzer according to claim 13, wherein the processor is programmed to output the first index value and the second index value to the display part.

15. The blood sample analyzer according to claim 13, wherein the processor is programmed to output, to the display part, a graph plotting the first coagulation time, the second coagulation time, and the third coagulation time.

16. The blood sample analyzer according to claim 13, wherein the processor is programmed to output, to the display part, reference information concerning whether the blood sample of the subject is a blood sample containing the direct anticoagulant.

17. The blood sample analyzer according to claim 16, wherein
- in a condition in which the first index value is equal to or above the first threshold and the second index value is equal to or above the second threshold, the reference information indicates that the blood sample of the subject is the blood sample containing the direct anticoagulant, and
- in a condition in which the first index value is below the first threshold or in a condition in which the second index value is below the second threshold, the reference information indicates that the blood sample of the subject is a blood sample with a cause of coagulation abnormality other than the direct anticoagulant.

18. The blood sample analyzer according to claim 16, wherein
- in a condition in which the first index value is equal to or above the first threshold and the second index value is below the second threshold, the reference information indicates that the blood sample of the subject is a blood sample containing the lupus anticoagulant, and
- in a condition in which the first index value is below the first threshold and the second index value is below the second threshold, the reference information indicates that the blood sample of the subject is a blood sample deficient in a coagulation factor.

* * * * *